(12) United States Patent
Gross et al.

(10) Patent No.: US 10,905,701 B2
(45) Date of Patent: *Feb. 2, 2021

(54) COMPOSITIONS AND METHODS FOR INHIBITING ARGINASE ACTIVITY

(71) Applicant: CALITHERA BIOSCIENCES, INC., South San Francisco, CA (US)

(72) Inventors: Matthew I. Gross, Walnut Creek, CA (US); Susanne M. Steggerda, San Francisco, CA (US); Weiqun Li, Foster City, CA (US)

(73) Assignee: CALITHERA BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,403

(22) Filed: Jul. 29, 2019

(65) Prior Publication Data
US 2019/0343852 A1 Nov. 14, 2019

Related U.S. Application Data

(60) Continuation of application No. 16/113,816, filed on Aug. 27, 2018, now Pat. No. 10,398,714, which is a division of application No. 15/190,653, filed on Jun. 23, 2016, now Pat. No. 10,143,699.

(60) Provisional application No. 62/183,524, filed on Jun. 23, 2015.

(51) Int. Cl.
| | | |
|---|---|---|
| *A61K 31/69* | (2006.01) | |
| *A61K 39/00* | (2006.01) | |
| *A61K 45/06* | (2006.01) | |
| *C07K 16/28* | (2006.01) | |
| *G01N 33/50* | (2006.01) | |
| *A61K 39/395* | (2006.01) | |

(52) U.S. Cl.
CPC ........ *A61K 31/69* (2013.01); *A61K 39/39541* (2013.01); *A61K 45/06* (2013.01); *C07K 16/2818* (2013.01); *G01N 33/5011* (2013.01); *G01N 33/5023* (2013.01); *A61K 2039/505* (2013.01); *G01N 2800/52* (2013.01)

(58) Field of Classification Search
CPC ........ A61K 31/69; A61K 39/00; A61K 45/06; C07K 16/28
See application file for complete search history.

(56) References Cited

U.S. PATENT DOCUMENTS

| | | |
|---|---|---|
| 8,894,970 B2 | 11/2014 | Tomczuk et al. |
| 9,200,011 B2 | 12/2015 | Van Zandt et al. |
| 9,233,985 B2 | 1/2016 | Van Zandt et al. |
| 9,266,908 B2 | 2/2016 | Van Zandt et al. |
| 9,440,995 B2 | 9/2016 | Van Zandt et al. |
| 2002/0081626 A1 | 6/2002 | Kaddurah-Daouk et al. |
| 2004/0063666 A1 | 4/2004 | Christianson et al. |
| 2010/0189644 A1 | 7/2010 | Christianson et al. |
| 2012/0083469 A1 | 4/2012 | Van Zandt et al. |
| 2012/0129806 A1 | 5/2012 | Van Zandt et al. |
| 2014/0371175 A1 | 12/2014 | Van Zandt et al. |
| 2015/0080341 A1 | 3/2015 | Van Zandt et al. |
| 2015/0191492 A1 | 7/2015 | Van Zandt et al. |
| 2016/0375044 A1 | 12/2016 | Gross et al. |

FOREIGN PATENT DOCUMENTS

| | | |
|---|---|---|
| CA | 2431080 A1 | 12/2004 |
| CN | 103068830 A | 4/2013 |
| CN | 103402549 A | 11/2013 |
| CN | 105879030 A | 8/2016 |
| JP | 2015516397 A | 6/2015 |
| WO | 1999019295 A1 | 4/1999 |
| WO | 2007005620 A2 | 1/2007 |
| WO | 2010085797 A2 | 7/2010 |
| WO | 2011133653 A1 | 10/2011 |
| WO | 2012058065 A1 | 5/2012 |
| WO | 2012091757 A1 | 7/2012 |
| WO | 2013059587 A1 | 4/2013 |
| WO | 2013158262 A1 | 10/2013 |
| WO | 2015061752 A1 | 4/2015 |
| WO | 2016153078 A1 | 9/2016 |
| WO | 2016210106 A1 | 12/2016 |

OTHER PUBLICATIONS

Peggs et al., "Blockade of CTLA-4 on both effector and regulatory T cell compartments contributes to the antitumor activity of anti-CTLA-4 antibodies," J. Exp. Med. vol. 206 No. 8 1717-1725.
Yang et al., "Ipilimumab (Anti-CTLA4 Antibody) Causes Regression of Metastatic Renal Cell Cancer Associated With Enteritis and Hypophysitis," J Immunother. 2007; 30(8): 825-830.
Ajinomoto Amino Acids Link News Aug. 2005 vol. 11: 3-4.
Arina, A. et al. 2014 "Adoptively Transferred Immune T Cells Eradicate Established Tumors despite Cancer-Induced Immune Suppression," J Immunol 192: 1286-1293.
Baggio et al. 1997 "Inhibition of Mn2+ 2-Arginase by Borate Leads to the Design of a Transition State Analogue Inhibitor, 2(S)-Amino-6-boronohexanoic Acid," J Am Chem Soc 119(34): 8107-8108.
Barbul, A. 1990 "Arginine and Immune Function," Nutrition 6(1) 53-58.
Bartolucci et al. 2012 "Direct, Regioselective and Chemoselective Preparation of Novel Boronated Tryptophans by Friedel-Crafts Alkylation" Organic Letters 14(2): 600-603.
Busnel et al. 2005 "Synthesis and evaluation of new co-borono-α-amino acids as rat liver arginase inhibitors," Bioorg Med Chem 13(7): 2373-2379.
Calithera Biosciences, Inc. Poster, SITC Conference; Nov. 9-13, 2016; National Harbor, MD.
Calithera Biosciences, Inc. Poster, EORTC-NCI-AACR; Nov. 29-Dec. 2, 2016; Munich, Germany.

(Continued)

*Primary Examiner* — Shirley V Gembeh
(74) *Attorney, Agent, or Firm* — Carl A. Morales; Seth E. Snyder; Dechert LLP

(57) ABSTRACT

The invention relates to methods of treating cancer, with a combination of an arginase inhibitor and a chemotherapeutic agent. The invention further relates to methods of assessing efficacy of a cancer treatment by measuring arginine levels in a tumor.

30 Claims, 4 Drawing Sheets

(56) References Cited

OTHER PUBLICATIONS

Figure 1:
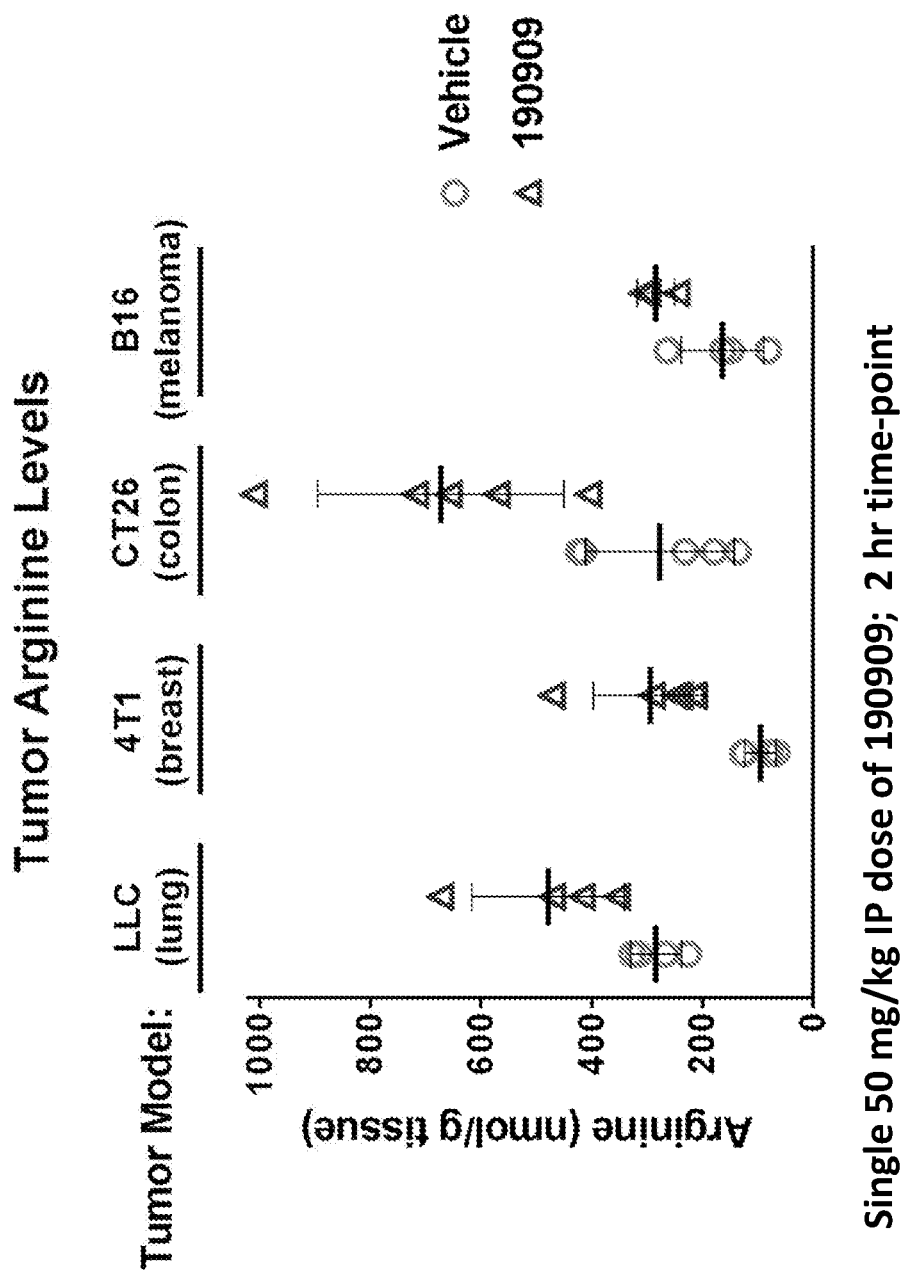

CAS Registry No. 1374395-07-9. CA Index Name: "3-Pyrrolidinecarboxylic acid, 3-amino-4-(3-boronopropyl)-14(5,7-dichloro-1,2,3,4-tetrahydro-3-isoquinolinyl)carbonyll-, (3R,4S)-rel-". STN Entry Date: May 24, 2012 (Last update: May 28, 2012).
Colleluori et al. 2001 "Classical and Slow-Binding Inhibitors of Human Type II Arginase," Biochem, 40(31): 9356-9362.
Curtis, B. et al. 2013 "Secondary amines containing one aromatic nitro group: preparation, nitrosation, sustained nitric oxide release, and the synergistic effects of released nitric oxide and an arginase inhibitor on vascular smooth muscle cell proliferation," Bioorganic & medicinal chemistry 21(5) 1123-1135. Retrieved from: <https://www.ncbi.nlm.nih.gov/pmc/articles/PMC3574223/pdf/nihms434525.pdf>.
Ellyard et al. 2010 "Alternatively Activated Macrophage Possess Antitumor Cytotoxicity That is Induced by IL-4 and Mediated by Arginase-1," J Immunother 33: 443-452.
Geiger, R. et al. 2016 "L-Arginine Modulates T Cell Metabolism and Enhances Survival and Anti-tumor Activity," Cell, Cell Press 167(3): 829ff.
Gritli-Linde, A. et al. 1998 "Opposing effects of suramin and DL-alpha-difluoromethylornithine on polyamine metabolism contribute to a synergistic action on B16 melanoma cell growth in vitro," Anticancer Research 18(2A) 863-870.
Hörig et al. 2004 "From bench to clinic and back: Perspective on the 1st IQPC Translational Research conference," J Translational Med, 2:44 doi:10.1186/1479-5876-2-44.
Ilies et al. 2011 "Binding of alpha,alpha-Disubstituted Amino Acids to Arginase Suggests New Avenues for Inhibitor Design," J Med Chem 54(15): 5432-5443.
International Preliminary Report on Patentability for International Application No. PCT/US2011/033223 dated Oct. 23, 2012. [CBH-012.25].
International Preliminary Report on Patentability for International Application No. PCT/US2013/030930 dated Oct. 30, 2014. [CBH-014.25].
International Search Report and Written Opinion for International Application No. PCT/US2011/033223 dated Jul. 14, 2011. [CBH-012.25].
International Search Report and Written Opinion for International Application No. PCT/US2011/056844 dated Dec. 14, 2011. [CBH-013.25].
International Search Report and Written Opinion for International Application No. PCT/US2012/060789 dated Dec. 19, 2012. [CBH-011.25].
International Search Report and Written Opinion for International Application No. PCT/US2013/030930 dated May 23, 2013. [CBH-014.25].
International Search Report and Written Opinion for International Application No. PCT/US2016/038983 dated Dec. 29, 2016.
International Preliminary Report on Patentability for International Application No. PCT/US2016/038983 dated Dec. 26, 2017.
Ivanenkov et al. 2014 "Small-molecule arginase inhibitors," Pharm Pat Anal 3(1): 65-85.
Kabalka et al. 2008 "Synthesis of a series of boronated unnatural cyclic amino acids as potential boron neutron capture therapy agents," Appl Organomet Chem, 22(9): 516-522.
Koziara et al. 2004 "Paclitaxel nanoparticles for the potential treatment of brain tumors," J Controlled Release 99: 259-269.
Lei et al. 2009 "Progress of Boronic Acids as Enzyme Inhibitors" Chinese J Pharm 40(3): 213-219 (English Abstract only).
Li L. et al. "An Engineered Arginase FC Protein Inhibits Tumor Growth In Vitro and In Vivo," Evidence-Based Complementary and Alternative Medicine vol. 2013, Article ID 243129: 1-9.
Lorvik, Kristina Berg et al. 2016 "Adoptive Transfer of Tumor-Specific Th2Cells Eradicates Tumors by Triggering an in Situ Inflammatory Immune Response," Cancer Research 76(23): 6864-6876.
Raber, P. et al. 2012 Metabolism of L-Arginine by Myeloid-Derived Suppressor Cells in Cancer: Mechanisms of T cell suppression and Therapeutic Perspectives Immunol Invest 41(6-7): 614-634.
Raber, P. et al. 2016 "T cells conditioned with MDSC show an increased anti-tumor activity after adoptive T cell base immunotherapy," Oncotarget 7(14): 17565-17578.
Rodriguez, P. et al. 2003 "L-Arginine Consumption by Macrophages Modulates the Expression of CD3zeta Chain in T Lymphocytes," J Immunol 171, 1232-1239.
Rodriguez, P. et al. 2004 "Arginase I Production in the Tumor Microenvironment by Mature Myeloid Cells Inhibits T-Cell Receptor Expression and Antigen-Specific T-Cell Responses," Cancer Research 64: 5839-5849.
Rodriguez, P. et al. 2008 "Arginine regulation by myeloid derived suppressor cells and tolerance in cancer: mechanisms and therapeutic perspectives," Immunol Rev 222: 180-191.
Rossnagl, Stephanie et al. 2016, "EDA-Fibronectin Originating from Osteoblasts Inhibits the Immune Response against Cancer," PLOS Biology 14(9): e1002562.
Sandgren, S. and Belting, M. 2003 "Suramin Selectively inhibits carcinoma cell growth that is dependent on extracellular polyamines," Anticancer Research 23(26): 1223-1228.
Schafer, et al. 2008 "Failure is an option: learning from unsuccessful proof-of-concept trials," Drug Discov Today, 13(21): 913-916.
Scheit, K. and Bauer, G. 2014 "Synergistic effects between catalase inhibitors and modulators of nitric oxide metabolism on tumor cell apoptosis," Anticancer Research 34(10): 5337-5350. Retrieved from: <https://ar.iiarj ournals.org/content/34/10/5337. full.pdf+html>.
Segal et al. 2012 "Chronic Oral Administration of the Arginase Inhibitors 2(S)-amino-6-boronohexanoic Acid (ABH) Improves Erectile Function in Aged Rates," J Androl, 33(6): 1169-1175.
Selamnia, M. et al. 1998 "?-Difluoromethylornithine (DFMO) as a potent arginase activity inhibitor in human colon carcinoma cells," Biochemical pharmacology 55(8): 1241-1245.
Singh, S. et al. 2000 "Arginase Activity in Human Breast Cancer Cell Lines: N?-Hydroxy-L-arginine Selectively Inhibits Cell Proliferation and Induces Apoptosis in MDA-MB-468 Cells" Cancer Research 60: 3305-3312.
Steggerda, S. M. et al. 2016 "Abstract B045: Arginase inhibitor CB-1158 elicits immune-mediated antitumor responses as a single agent and in combination with other immunotherapies," Second CRI-CIMT-EATI-AACR International Cancer Immunotherapy Conference: Translating Science into Survival; Sep. 25-28, 2016; New York, NY.
Steggerda, S. M. et al. 2017, "Inhibition of arginase by CB-1158 blocks myeloid cell-mediated immune suppression in the tumor microenvironment," Journal for ImmunoTherapy of Cancer 5(1): 1-18.
Tate et al. 2008 "Effect of arginase II on L-arginine depletion and cell growth in murine cell lines of renal cell carcinoma," J Hematol Oncol 1(14): 1-10.
Vissers, Y. et al. 2005 "Plasma arginine concentrations are reduced in cancer patients: evidence for arginine deficiency?" Am J Clin Nutr 81: 1142-1146.
Liu, Y. et al., "Regulation of arginase I activity and expression by both PD-1 and CTLA-4 on the myeloid-derived suppressor cells," Cancer Immunology, Immunotherapy, 2009, vol. 58, No. 5, p. 687-697.

COMPOSITIONS AND METHODS FOR INHIBITING ARGINASE ACTIVITY

CROSS REFERENCE TO RELATED APPLICATIONS

This application is a continuation of U.S. application Ser. No. 16/113,816, filed Aug. 27, 2018, now U.S. Pat. No. 10,398,714, which is a division of U.S. application Ser. No. 15/190,653, filed Jun. 23, 2016, now U.S. Pat. No. 10,143,699, which claims the benefit of priority to U.S. Provisional Patent Application No. 62/183,524, filed Jun. 23, 2015, the contents of each of which are incorporated herein by reference in their entireties.

BACKGROUND

Cancer is characterized by the uncontrolled growth of cells in the body, leading to the invasion of essential organs and often death. Initially, the pharmacological treatment of cancer utilized non-specific cytotoxic agents that targeted all rapidly dividing cells, including normal cells. These non-specific cytotoxic agents have anti-tumor effects but their use is often limited by severe toxicities. As the understanding of the proteins and pathways that enable cancer cells to thrive has evolved, newer more targeted agents have been developed that block specific proteins that are activated in cancer cells.

An emerging field for the development of therapeutics that addresses the challenges presented in treating cancers is immune-oncology, also referred to as tumor immunology. Certain tumor types have developed mechanisms to escape destruction by the body's immune system. Tumor immunology is a therapeutic area focused on activating the body's own immune system to attack and kill tumors. The naturally occurring amino acid arginine is implicated in tumor immunology, as it is important for the activation, growth, and survival of a body's cancer-fighting cytotoxic T-cells. However, levels of arginine are depleted in the tumor microenvironment by arginase, an enzyme produced and secreted by myeloid derived suppressor cells (MDSCs) that accumulate in cancer patients of multiple histotypes. In fact, elevated levels of arginase enzyme have been observed in the plasma of renal cell carcinoma, breast cancer, chronic myelogenous leukemia, esophageal cancer, prostate cancer, non-small cell lung cancer, glioblastoma, and acute myeloid leukemia patients. Therefore, there is a need to develop inhibitors of arginase that restore arginine levels in the tumor microenvironment, therefore promoting the tumor-killing activity of cytotoxic T-cells.

SUMMARY OF INVENTION

In certain aspects, the invention provides methods for identifying a therapeutic agent effective to increase the level of arginine in a tumor, comprising:
a) measuring a first level of arginine in a tumor;
b) contacting the tumor with a therapeutic agent; and
c) measuring a second level of arginine in the tumor;
wherein when the second level of arginine is higher than the first level of arginine, then the therapeutic agent is effective to increase the level of arginine in the tumor.

In certain aspects, the invention provides methods of identifying a therapeutic agent effective to increase the level of arginine in a tumor in a subject, comprising:
a) measuring a first level of arginine in a tumor of a subject;
b) administering to the subject a therapeutic agent; and
c) measuring a second level of arginine in the tumor of the subject;
wherein when the second level of arginine is higher than the first level of arginine, then the therapeutic agent is effective to increase the level of arginine in the tumor of the subject.

In other aspects, the present invention provides methods of assessing a response of a tumor to an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the response of the tumor to the agent of arginine therapy.

The invention also provides methods for assessing the anti-cancer efficacy of an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the anti-cancer efficacy of an agent of arginine therapy.

The invention further provides methods for treating or preventing cancer, comprising administering to a subject in need thereof a therapeutically effective amount of an agent of arginine therapy. The agent of arginine therapy may be an arginase inhibitor, such as a compound of any of Formulae I, II, or III. In certain embodiments, the methods further comprise conjointly administering one or more additional chemotherapeutic agents.

Also provided are methods of assessing the anti-cancer efficacy of a combination therapy regimen, comprising:
a) measuring a first level of arginine in a tumor of a cancer patient;
b) conjointly administering to the patient an agent of arginine therapy and one or more additional chemotherapeutic agents; and
c) measuring a second level of arginine in the tumor of the patient, thereby assessing the anti-cancer efficacy of the combination therapy regimen.

The invention further provides pharmaceutical kits, comprising a chemotherapeutic agent, an arginase inhibitor (such as a compound of any one of Formulae I, II, or III, and optionally directions on how to administer the chemotherapeutic agent and arginase inhibitor.

DETAILED DESCRIPTION OF THE DRAWINGS

FIG. 1 depicts the restoration of arginine in tumors from mouse models of lung cancer, breast cancer, colon cancer, and melanoma. A single dose of arginase inhibitor compound 190909 increased the level of arginine in the tumor microenvironment relative to vehicle (control) for multiple cancer types.

Figure 2:
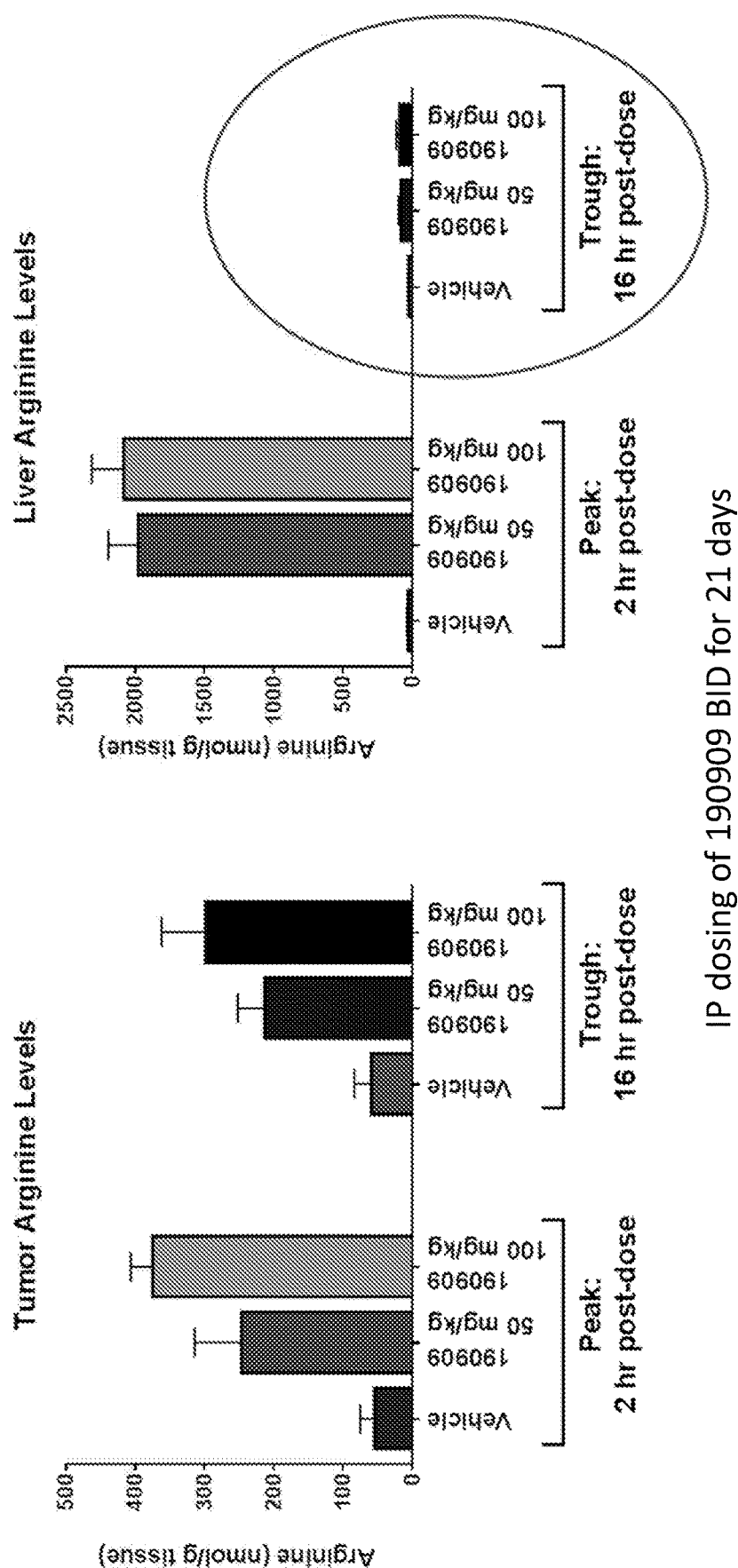

FIG. 2 contains a series of bar graphs that demonstrate that arginase inhibitor compound 190909 restores arginine levels in the tumor microenvironment but not in liver tissue at a time point of 16 hours after dosing. These findings demonstrate that the efficacy of compound 190909 does not come at the expense of general toxicity of the compound.

Figure 3:
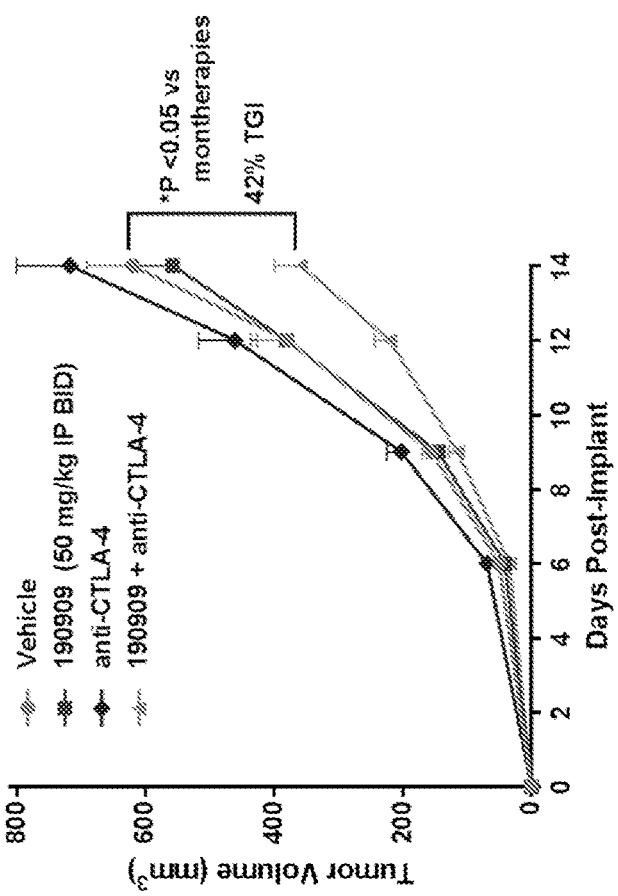
Figure 3:
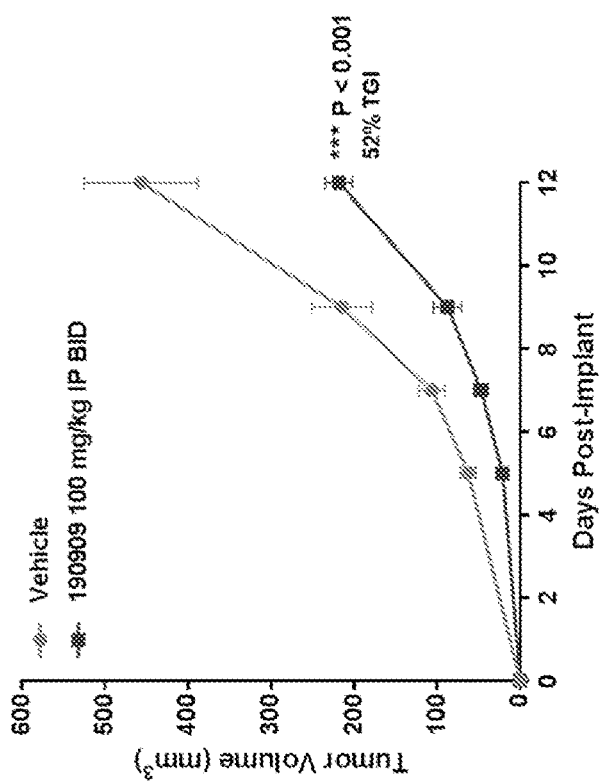

FIG. 3 contains two graphs that plot tumor volume over time. Arginase inhibitor compound 190909, administered as a single agent, slows tumor growth relative to vehicle (control). In combination with an anti-CTLA-4 antibody, however, compound 190909 slows tumor growth even more that single agent compound 190909.

Figure 4:
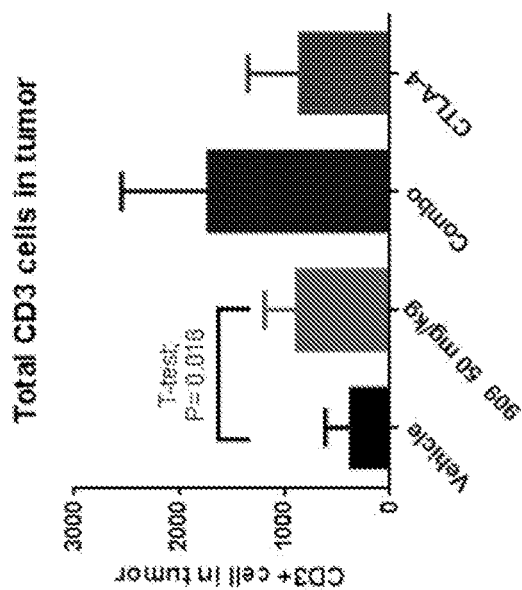
Figure 4:
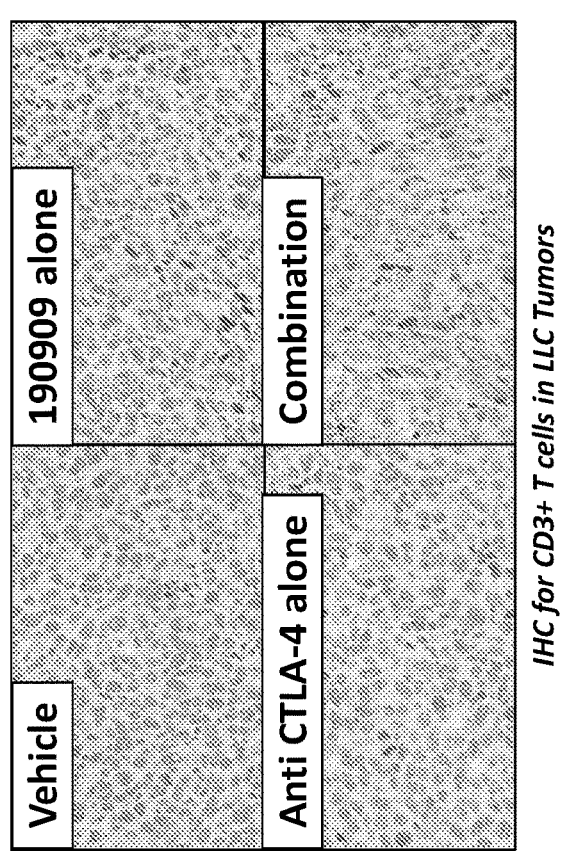

FIG. 4 consists of two panels, A and B, and shows a series of immunohistochemistry images of CD3+ T-cells in Lewis lung carcinoma (LLC) tumors after treatment with vehicle, single agent arginase inhibitor compound 190909, single agent anti-CTLA-4 antibody, and combination therapy with arginase inhibitor compound 190909 and anti-CTLA-4 antibody (panel A). T-cell infiltrate in LLC tumors is also represented graphically (panel B).

DETAILED DESCRIPTION OF THE INVENTION

The present invention is based on the surprising discovery that certain small molecule inhibitors of arginase, described herein, are effective to increase arginine levels in the tumor microenvironment. The present invention relates to the application of such arginase inhibitors to various therapeutic methods for cancer treatment.

Accordingly, the present invention provides a method of identifying a therapeutic agent effective to increase the level of arginine in a tumor, comprising:
a) measuring a first level of arginine in a tumor;
b) contacting the tumor with a therapeutic agent; and
c) measuring a second level of arginine in the tumor;
wherein when the second level of arginine is higher than the first level of arginine, then the therapeutic agent is effective to increase the level of arginine in the tumor.

In certain embodiments, this method is conducted in vitro. In alternative embodiments, this method is conducted in vivo.

In certain embodiments (e.g., when the method is conducted in vivo), the step of contacting the tumor with a therapeutic agent comprising administering the therapeutic agent to a subject. In certain embodiments, the subject can be a human.

A level of arginine may be measured, for example, by HPLC, mass spectrometry, LCMS, or other analytic techniques known to those of skill in the art. Example 5 describes arginine measurement by LCMS.

The invention also provides a method of identifying a therapeutic agent effective to increase the level of arginine in a tumor in a subject, comprising:
a) measuring a first level of arginine in a tumor of a subject;
b) administering to the subject a therapeutic agent; and
c) measuring a second level of arginine in the tumor of the subject;
wherein when the second level of arginine is higher than the first level of arginine, then the therapeutic agent is effective to increase the level of arginine in the tumor of the subject.

In certain embodiments, the step of administering comprises oral administration of the therapeutic agent. Alternatively, the step of administering can comprise parenteral administration of the therapeutic agent. Further methods of administration are discussed herein.

In certain embodiments, the subject is a human.

As used herein, the term "in a tumor" refers to the entire tumor mass and the tumor microenvironment. For example, the tumor mass can include, but is in no way limited to, cancer (tumorous) cells, T-cells, macrophages, and stromal cells. The "tumor microenvironment" is an art-recognized term and refers to the cellular environment in which the tumor exists, and includes, for example, surrounding blood vessels, immune cells, other cells, fibroblasts, signaling molecules, and the extracellular matrix. Therefore, measurement of arginine "in a tumor" refers to measurement of arginine in the tumor mass or in its microenvironment.

Accordingly, in certain embodiments of the methods described herein, the first and second levels of arginine are measured in the tumor cells.

In other embodiments, the first and second levels of arginine are measured in stromal cells associated with the tumor.

In certain embodiments, the therapeutic agent is an arginase inhibitor (e.g., a compound of Formula I, II, or III). Exemplary arginase inhibitors are described below.

In certain embodiments in which the therapeutic agent is effective to increase the level of arginine in a tumor, the therapeutic agent can be effective to treat the tumor.

In other embodiments, the present invention provides a method of assessing a response of a tumor to an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the response of the tumor to the agent of arginine therapy.

In certain embodiments, if the second level of arginine is higher than the first level of arginine, then the tumor is responsive to (i.e., is treated by) the agent of arginine therapy. An increase of arginine in a tumor mass or in the tumor microenvironment can indicate an increase in the number of cytotoxic T-cells or an increase in the activity of cytotoxic T-cells.

An "agent of arginine therapy" as used herein, means a therapeutic agent that can cause an increase in the level of arginine in the system of interest (e.g., a tumor mass and its microenvironment).

In certain embodiments, the agent of arginine therapy is an arginase inhibitor (e.g., a compound of Formula I, II, or III).

In other embodiments, the present invention provides a method of assessing the anti-cancer efficacy of an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the anti-cancer efficacy of an agent of arginine therapy.

In certain embodiments, when the second level of arginine is higher than the first level of arginine, then the agent of arginine therapy is efficacious for treating cancer in a patient.

In certain embodiments, the agent of arginine therapy is an arginase inhibitor.

The present invention also provides a method for treating or preventing cancer, comprising conjointly administering to a subject in need thereof a therapeutically effective amount of an agent of arginine therapy and one or more additional chemotherapeutic agents.

In certain embodiments, administering the agent of arginine therapy effects an increase in a level of arginine in a tumor of the subject relative to the level of arginine in the tumor prior to administration.

In certain embodiments, administering the agent of arginine therapy effects an increase in a level of arginine in the tumor cells of the subject relative to the level of arginine in the tumor cells prior to administration.

Similarly, administering the agent of arginine therapy may effect an increase in a level of arginine in stromal cells associated with the tumor of the subject relative to the level of arginine in the stromal cells prior to administration.

In certain embodiments, the agent of arginine therapy is an arginase inhibitor. A number of exemplary arginase inhibitors are described herein. In particular embodiments, the arginase inhibitor is a compound having the structure of any one of Formulae I, II, or III, which are described below.

In other embodiments, the invention provides methods for assessing the anti-cancer efficacy of a combination therapy regimen, comprising:

a) measuring a first level of arginine in a tumor of a cancer patient;
b) conjointly administering to the patient an agent of arginine therapy and one or more additional chemotherapeutic agents; and
c) measuring a second level of arginine in the tumor of the patient, thereby assessing the anti-cancer efficacy of the combination therapy regimen.

In certain embodiments, when the second level of arginine is higher than the first level of arginine, then the combination therapy regimen is efficacious for treating cancer in the patient.

In certain embodiments, the agent of arginine therapy used in the combination therapy regimen is an arginase inhibitor, such as a compound of any one of Formulae I, II, or III.

In certain embodiments, the combination therapy regimen is more efficacious than a therapy regimen of the arginase inhibitor as a single agent, or a therapy regimen of the additional chemotherapeutic agent as a single agent.

The invention also provides pharmaceutical kits comprising a chemotherapeutic agent, an arginase inhibitor, and optionally directions on how to administer the chemotherapeutic agent and arginase inhibitor.

Arginase Inhibitors for Use with the Invention

The present invention provides methods for treating or preventing cancer comprising conjointly administering to a subject in need thereof a therapeutically effective amount of an agent of arginine therapy and one or more additional chemotherapeutic agents.

In certain preferred embodiments of any of the methods described herein, the agent of arginine therapy is an arginase inhibitor.

In certain embodiments, the arginase inhibitor used in the methods of the invention is a compound having the structure of Formula I,

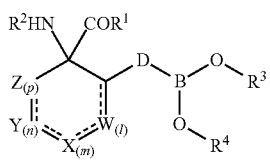

I wherein
$R^1$ is selected from —OH, $OR^a$, and $NR^bR^c$;
$R^a$ is selected from hydrogen, substituted or unsubstituted alkyl, cycloalkyl, aryl, (heterocycloalkyl)alkyl, (heteroaryl)alkyl, and aralkyl;
$R^b$ and $R^c$ are each independently selected from H, —OH, substituted or unsubstituted alkyl, —$SO_2$(alkyl), —$SO_2$(aryl), (heterocycloalkyl)alkyl, and (heteroaryl)alkyl;

$R^2$ is selected from H, substituted or unsubstituted alkyl, and (alkyl)C(O)—;
W, X, Y, and Z are each independently selected from a bond, —C(R)(R''')—, —C(R''')$_2$—, —CR'''—, —NR'''—, —N—, —O—, —C(O)—, and —S—, such that no more than three of W, X, Y, and Z simultaneously represent a bond; and no two adjacent members of W, X, Y, and Z are simultaneously —O—, —S—, —N—, or —NR'''—;
l, m, n and p are each independently 1 or 2;

optionally represents one or more double bonds;
$R^3$ and $R^4$ are each independently selected from hydrogen, substituted or unsubstituted alkyl, and C(O)—R', or
$R^3$ and $R^4$ together with the boron atom to which they are bound form a 5- or 6-membered ring that is fully saturated or partially saturated;
D is selected from substituted or unsubstituted alkylene, alkenylene, alkynylene, arylene, and cycloalkylene,
wherein one or more —$CH_2$— groups in D are optionally and independently replaced with a moiety Q that is selected from O, NR', S, SO, $SO_2$, and CR'R''; or
wherein any two adjacent —$CH_2$— groups optionally are replaced by two members of a cycloalkylenyl group (thereby forming a fused bicyclic system);
provided that D does not contain two adjacent Q moieties selected from O, NR', S, SO, and $SO_2$; and
R', R'' and R''' are each independently selected from H, OH, $S(O)R^d$, $S(O)_2R^d$, alkyl, aryl, —$NH_2$, —NH(alkyl), —N(alkyl)$_2$, —C(O)$NR^dR^e$, —C(O)(alkyl), —C(O)(aryl), —C(O)O(alkyl), —C(O)O(aryl), cycloalkyl, heterocycloalkyl, —C(O)(heterocycloalkyl), heteroaryl, aralkyl, —C(O)(aralkyl), —C(O)(aryl), (cycloalkyl)alkyl, (heteroaryl)alkyl-, and (heterocycloalkyl)alkyl;
wherein $R^d$ and $R^e$ are each independently selected from H, substituted or unsubstituted alkyl, aralkyl, aryl, hydroxyalkyl, aminoalkyl, cycloalkyl, heterocycloalkyl, heteroaryl, NR'R''C(O)—, and (aryl)cycloalkylene-,
wherein any alkyl, alkenyl, alkynyl, aryl, heteroaryl, cycloalkyl, or
heterocycloalkyl is optionally further substituted;
or a pharmaceutically acceptable salt, stereoisomer, tautomer, or prodrug thereof.

In certain embodiments of the compound of formula I,
$R^1$ is selected from —OH, $OR^a$, and $NR^bR^c$;
$R^a$ is selected from hydrogen, straight or branched chain ($C_1$-$C_6$)alkyl, ($C_3$-$C_8$)cycloalkyl, ($C_3$-$C_{14}$)aryl, ($C_3$-$C_{14}$)heterocycloalkyl-($C_1$-$C_6$)alkylene-, ($C_3$-$C_{14}$)heteroaryl-($C_1$-$C_6$)alkylene-, and ($C_3$-$C_{14}$)aryl ($C_1$-$C_6$)alkylene-;
$R^b$ and $R^c$ are each independently selected from H, —OH, straight or branched ($C_1$-$C_6$)alkyl, —$SO_2$—($C_1$-$C_6$)alkyl, ($C_3$-$C_{14}$)aryl-$SO_2$—, ($C_3$-$C_{14}$)heterocycloalkyl-($C_1$-$C_6$)alkylene-, and ($C_3$-$C_{14}$)heteroaryl-($C_1$-$C_6$)alkylene-;
$R^2$ is selected from H, straight or branched ($C_1$-$C_6$) alkyl, and ($C_1$-$C_6$)alkyl-C(O)—;
W, X, Y, and Z are each independently selected from a bond, —C(R')(R''')—, —C(R''')$_2$—, —CR'''—, —NR'''—, —N═, —O—, —C(O)—, and —S—, such that no more than three of W, X, Y, and Z simultaneously represent a bond; and no two adjacent members of W, X, Y, and Z are simultaneously —O—, —S—, ═N—, or —NR'''—;

l, m, n and p are each independently 1 or 2;

optionally represents one or more double bonds;

R$^3$ and R$^4$ are each independently selected from hydrogen, straight or branched (C$_1$-C$_6$)alkyl, and C(O)—R', or R$^3$ and R$^4$ together with the boron atom to which they are bound form a 5- or 6-membered ring that is fully saturated or partially saturated;

D is selected from straight or branched (C$_3$-C$_5$)alkylene, straight or branched (C$_2$-C$_8$)alkenylene, straight or branched (C$_2$-C$_8$)alkynylene, (C$_3$-C$_{14}$)arylene, and (C$_3$-C$_{14}$)cycloalkylene, wherein one or more —CH$_2$— groups in D are optionally and independently replaced with a moiety Q that is selected from O, NR', S, SO, SO$_2$, and CR'R''; wherein any two adjacent —CH$_2$— groups optionally are replaced by two members of a (C$_3$-C$_{14}$)-cycloalkylenyl group;

provided that D does not contain two adjacent Q moieties selected from O, NR', S, SO, and SO$_2$; and R', R'' and R''' are each independently selected from H, OH, S(O)R$^d$, S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)NR$^d$R$^e$, —C(O)(C$_1$-C$_6$)alkyl, —C(O)(C$_3$-C$_{14}$)aryl, —C(O)O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, —C(O)(C$_3$-C$_{14}$)heterocycloalkyl, (C$_3$-C$_{14}$)heteroaryl, (C$_3$-C$_{14}$)aryl-(C$_1$-C$_6$)alkylene-, —C(O)(C$_3$-C$_{14}$)aryl-(C$_1$-C$_6$)alkylene-, —C(O)(C$_3$-C$_{14}$)aryl, (C$_3$-C$_6$)cycloalkyl-(C$_1$-C$_6$)alkylene-, (C$_3$-C$_{14}$)heteroaryl-(C$_1$-C$_6$)alkylene-, and (C$_3$-C$_{14}$)heterocycle-(C$_1$-C$_6$)alkylene-;

wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy;

wherein R$^d$, R$^e$, R$^g$, and R$^h$ are each independently selected from H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, NR'R''C(O)—, and (C$_3$-C$_6$)aryl-(C$_3$-C$_{14}$)-cycloalkylene-.

In further embodiments of the compound of Formula I, R$^1$ is selected from —OH, OR$^a$, and NR$^b$R$^c$;

R$^a$ is selected from hydrogen, straight or branched chain (C$_1$-C$_6$)alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl(C$_1$-C$_6$)alkylene-;

R$^b$ and R$^c$ are each independently selected from H, —OH, straight or branched (C$_1$-C$_6$)alkyl, —SO$_2$—(C$_1$-C$_6$)alkyl, (C$_3$-C$_{14}$)aryl-SO$_2$—, (C$_3$-C$_{14}$)heterocycloalkyl-(C$_1$-C$_6$)alkylene-, and (C$_3$-C$_{14}$)heteroaryl-(C$_1$-C$_6$)alkylene-;

R$^2$ is selected from H, straight or branched (C$_1$-C$_6$) alkyl, and (C$_1$-C$_6$)alkyl-C(O)—;

W, X, Y, and Z are each independently selected from a bond, —C(R''')$_2$—, ═CR'''—, —NR'''—, ═N—, —O—, —C(O)—, and —S—, such that no more than three of W, X, Y, and Z simultaneously represent a bond; and no two adjacent members of W, X, Y, and Z are simultaneously —O—, —S—, ═N—, or —NR'''—;

l, m, n and p are each independently 1 or 2;

optionally represents one or more double bonds;

R$^3$ and R$^4$ are each independently selected from hydrogen, straight or branched (C$_1$-C$_6$)alkyl, and C(O)—R', or R$^3$ and R$^4$ together with the boron atom to which they are bound form a 5- or 6-membered ring that is fully saturated or partially saturated;

D is selected from straight or branched (C$_3$-C$_5$)alkylene, straight or branched (C$_2$-C$_8$)alkenylene, straight or branched (C$_2$-C$_8$)alkynylene, (C$_3$-C$_{14}$)arylene, and (C$_3$-C$_{14}$)cycloalkylene, wherein one or more —CH$_2$— groups in D are optionally and independently replaced with a moiety Q that is selected from O, NR', S, SO, SO$_2$, and CR'R''; or wherein any two adjacent —CH$_2$— groups optionally are replaced by two members of a (C$_3$-C$_{14}$)-cycloalkylenyl group;

provided that D does not contain two adjacent Q moieties selected from O, NR', S, SO, and SO$_2$; and R', R'' and R''' are each independently selected from H, OH, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)(C$_1$-C$_6$)alkyl, —C(O)(C$_3$-C$_{14}$)aryl, —C(O)O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, (C$_3$-C$_{14}$)heteroaryl, (C$_3$-C$_{14}$)aryl-(C$_1$-C$_6$)alkylene-, (C$_3$-C$_6$)cycloalkyl-(C$_1$-C$_6$)alkylene-, (C$_3$-C$_{14}$)heteroaryl-(C$_1$-C$_6$)alkylene-, and (C$_3$-C$_{14}$)heterocycle-(C$_1$-C$_6$)alkylene-;

wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkoxy, and (C$_3$-C$_{14}$)aryloxy;

wherein R$^d$, R$^e$, R$^g$, and R$^h$ are each independently selected from H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, NR'R''C(O)—, and (C$_3$-C$_6$)aryl-(C$_3$-C$_{14}$)-cycloalkylene-.

In certain embodiments of the compound of Formula I, D is selected from:

-L$^1$-L$^2$-CH$_2$—CH$_2$—,
—CH$_2$-L$^1$-L$^2$-CH$_2$—
—CH$_2$—CH$_2$-L$^1$-L$^2$,
-L$^1$-CH$_2$—CH$_2$-L$^2$-,
-L$^1$-CH$_2$-L$^2$-CH$_2$—,

—CH$_2$-L$^1$-CH$_2$-L$^2$-,
-L$^1$-CH$_2$—CH$_2$—,
—CH$_2$-L$^1$-CH$_2$,
—CH$_2$—CH$_2$-L$^1$,
-L$^2$-CH$_2$—CH$_2$—,
—CH$_2$-L$^2$-CH$_2$—, and
—CH$_2$—CH$_2$-L$^2$, wherein L$^1$ and L$^2$ are independently selected from O, NR', S, SO, SO$_2$, and CR'R''; and when L$^1$ and L$^2$ are adjacent to each other, then L$^1$ and L$^2$ are not simultaneously O, NR', S, SO, or SO$_2$.

In certain embodiments, D is straight or branched (C$_3$-C$_5$)alkylene. In certain preferred embodiments, D is propylene.

In certain embodiments, R$^1$ is —OH.

In certain embodiments, each of R$^2$, R$^3$ and R$^4$ is hydrogen.

In certain embodiments, the arginase inhibitor is a carbocyclic-based structure.

Accordingly, in certain such embodiments, each of W, X, Y and Z is —C(R''')$_2$—.

Alternatively, in certain such embodiments, at least two of W, X, Y and Z is —CR''', and

represents one or more double bonds. In other alternative embodiments, each of W, X, Y and Z is —CR''', and

represents one or more double bonds.

In certain embodiments, wherein R''' is H. In alternative embodiments, at least one occurrence of R''' is not H.

In certain embodiments, the arginase inhibitor is a carbocyclic-based structure having from 3 to 10, 3 to 8, 4 to 8, 4 to 7, 5 to 7, or 5 to 6 ring atoms. In certain such embodiments, l+m+n+p=3. In other embodiments, l+m+n+p=4.

In certain embodiments, the arginase inhibitor is a heterocyclic-based structure. Accordingly, in certain such embodiments, at least one of W, X, Y, or Z is selected from —NR'''—, —N—, —O—, and —S—.

In certain embodiments, any one of W, X, Y and Z is —NH— and each instance of the remaining three is —C(R''')$_2$—. In certain such embodiments, X is NH.

In certain embodiments, wherein R''' is H. In alternative embodiments, at least one occurrence of R''' is not H.

The heterocyclic-based structure may optionally contain unsaturation. In certain embodiments, any one of W, X, Y and Z is —N— and at least one of the remaining three is —CR'''—, and

represents one or more double bonds. In certain embodiments, any one of W, X, Y and Z is —N— and each of the remaining three is —CR'''—, and

represents one or more double bonds.

In certain embodiments, X is —N—.

In certain embodiments, wherein R''' is H. In alternative embodiments, at least one occurrence of R''' is not H.

In certain embodiments, the arginase inhibitor is a heterocyclic-based structure having from 3 to 10, 3 to 8, 4 to 8, 4 to 7, 5 to 7, or 5 to 6 ring atoms. In certain embodiments, the sum of l, m, n, and p is 3, 4, 5, or 6. In certain embodiments, l+m+n+p=4.

In certain embodiments, the arginase inhibitor is not 1-amino-2-(3-boronopropyl)cyclohexane carboxylic acid.

In certain embodiments, the arginase inhibitor for use with the methods of the invention is selected from the following:

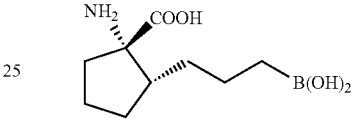
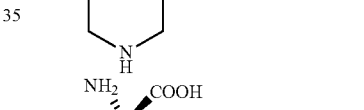
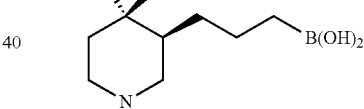
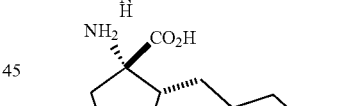
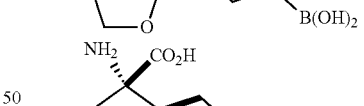
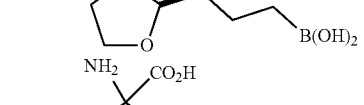
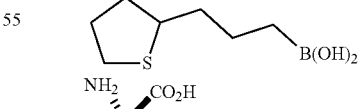
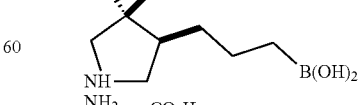
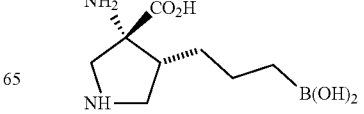

-continued
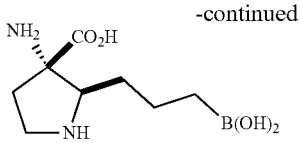
or a pharmaceutically acceptable salt, stereoisomer, or prodrug thereof.
In certain embodiments, the arginase inhibitor for use with the methods of the invention is selected from the following:
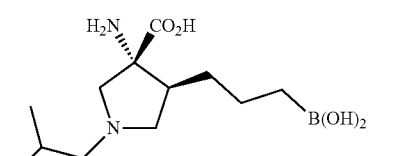
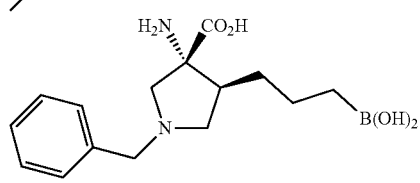
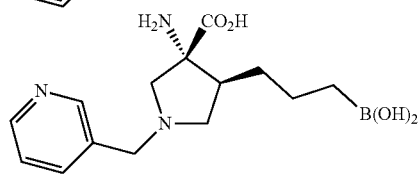
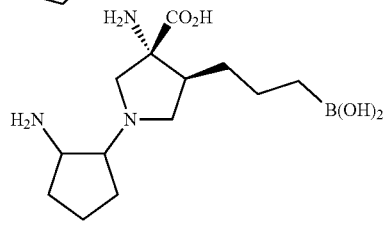
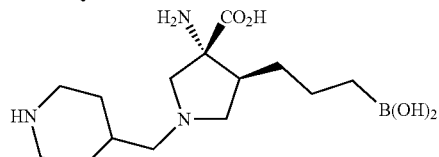
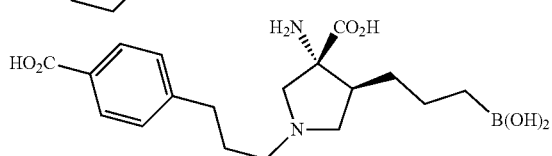
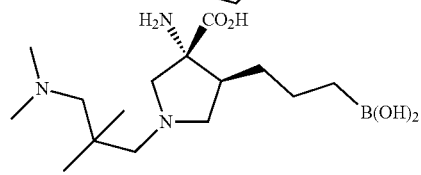
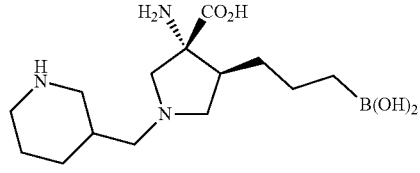
-continued
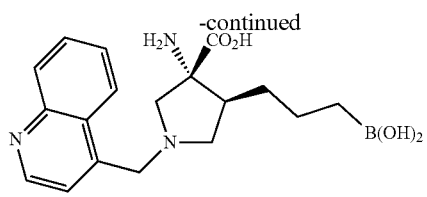
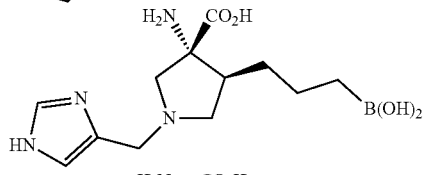
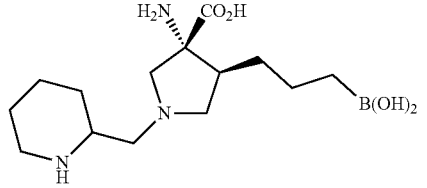
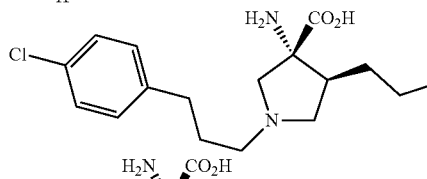
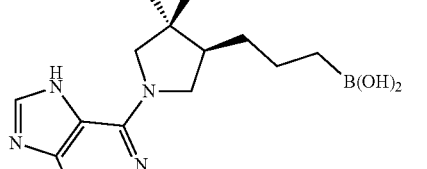
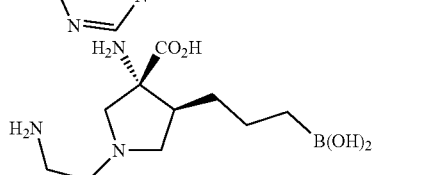
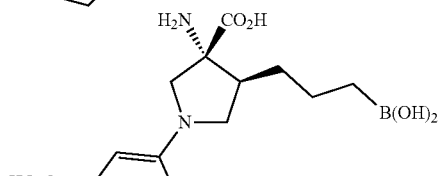
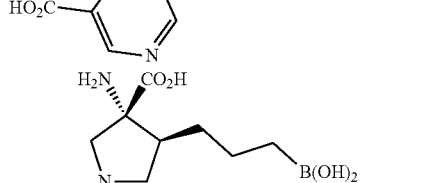
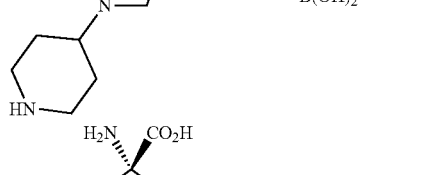
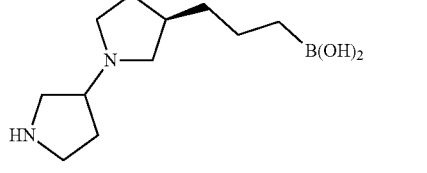

-continued
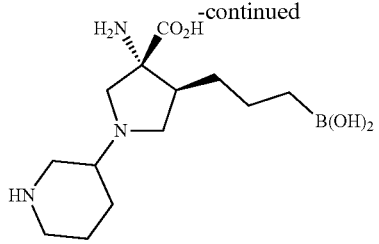
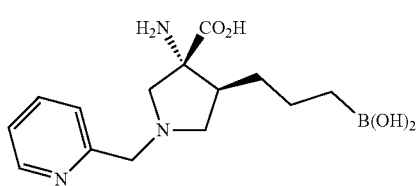
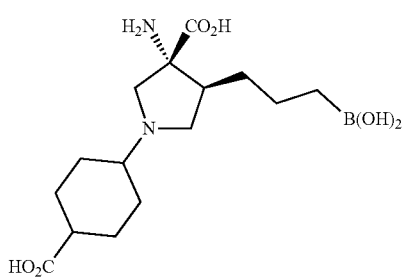
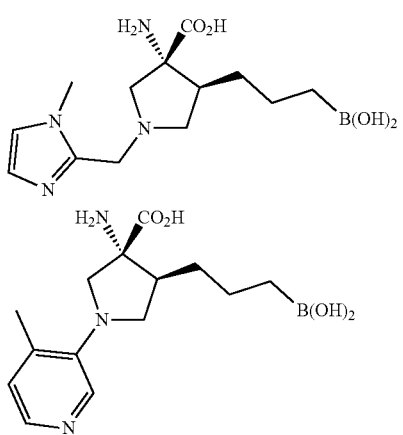
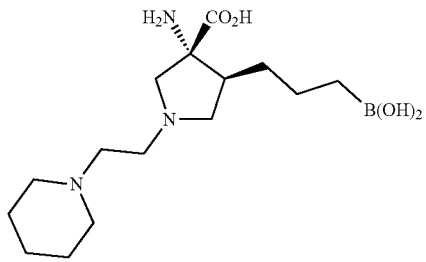
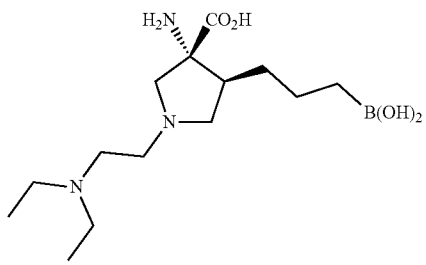
-continued
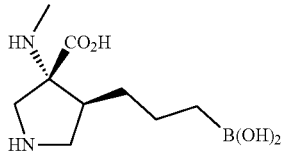
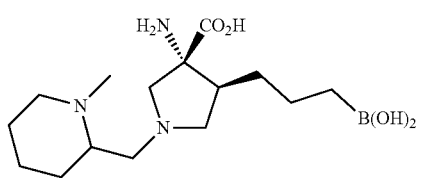
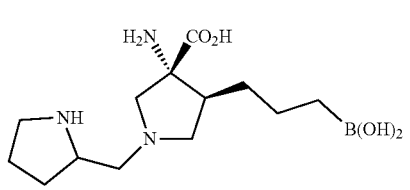
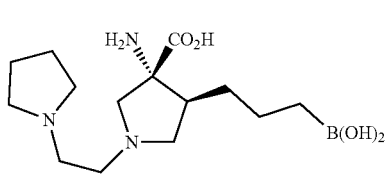
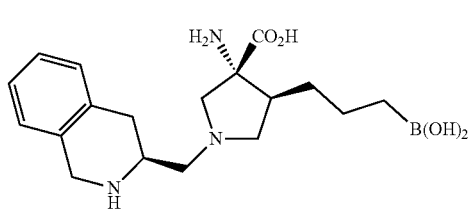
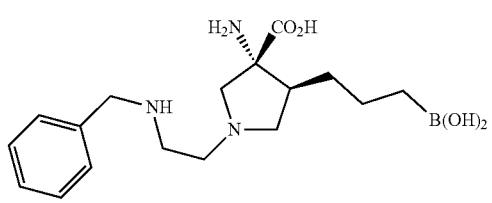
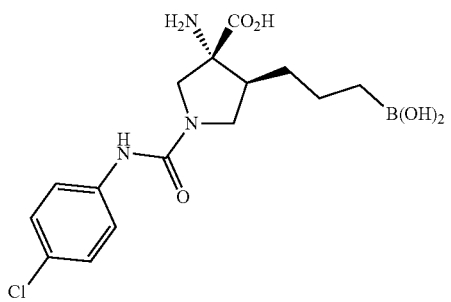
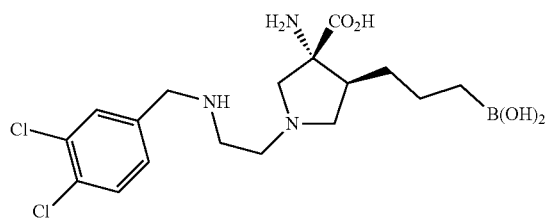

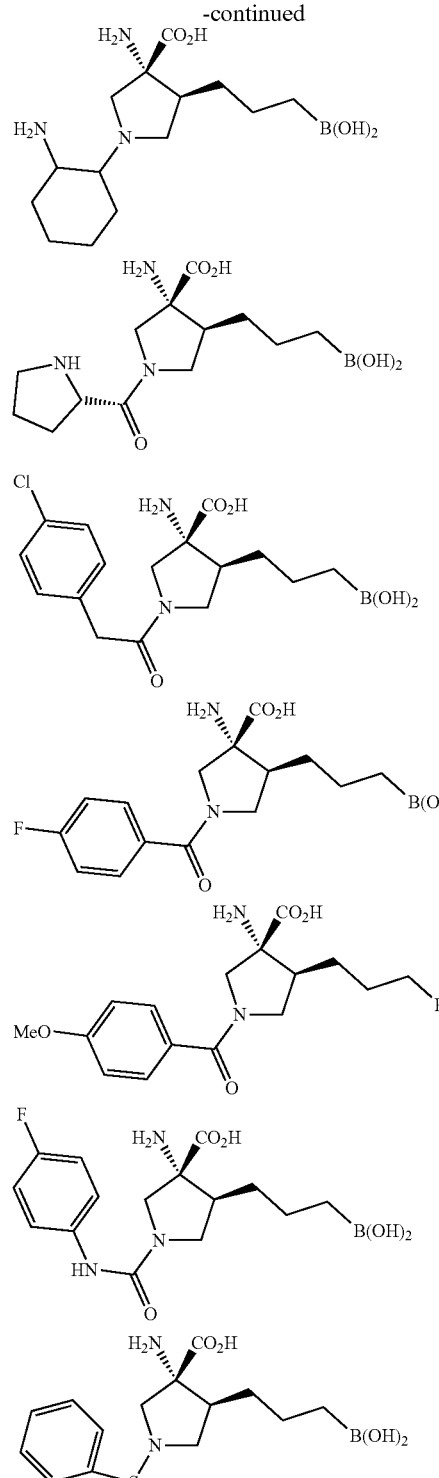
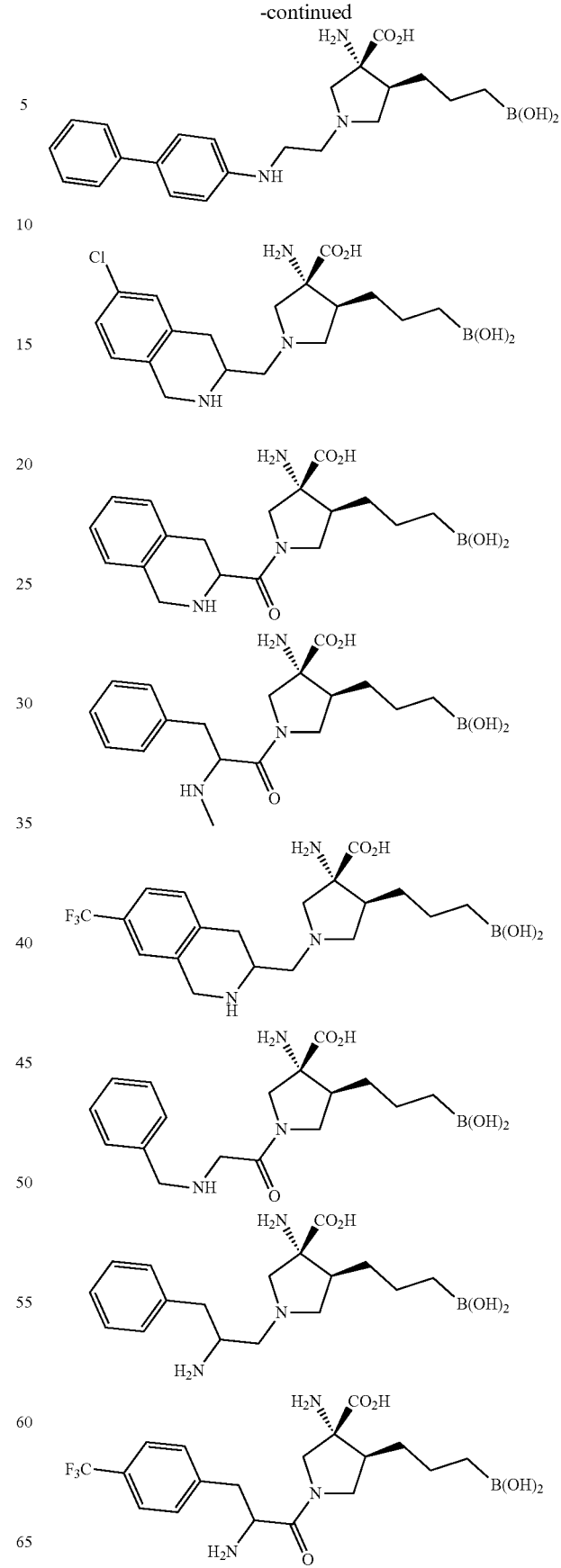

-continued

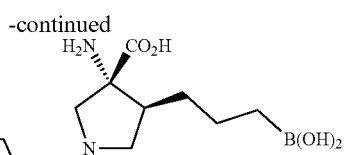
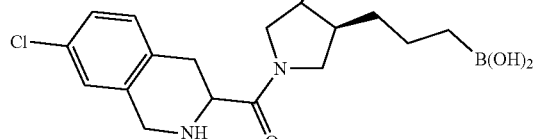
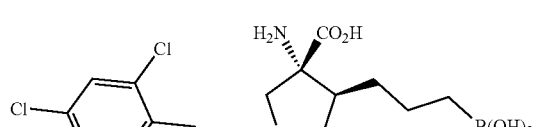
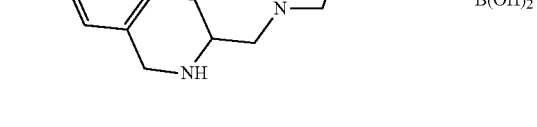
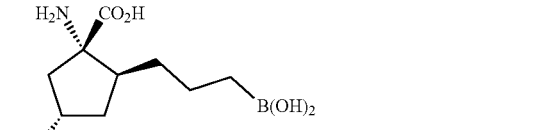
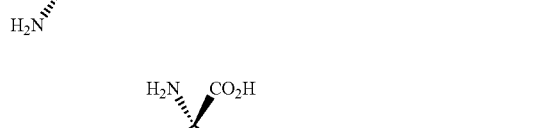
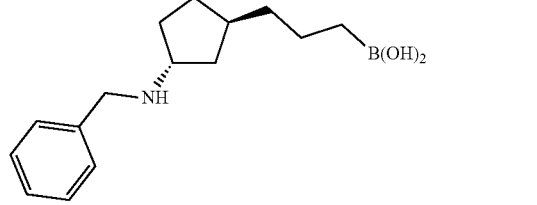
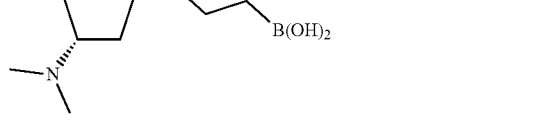
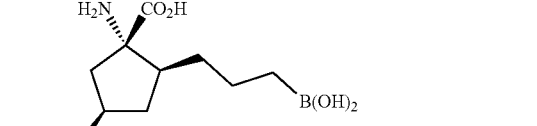
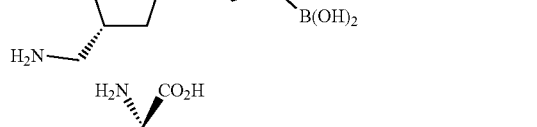
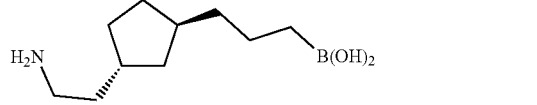

or a pharmaceutically acceptable salt, stereoisomer, or prodrug thereof.

In certain embodiments, the arginase inhibitor used in the methods of the invention is a compound having the structure of Formula II,

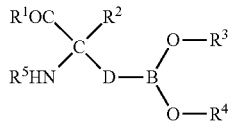

II wherein:
$R^1$ is selected from —OH, $OR^a$, and $NR^bR^c$;
$R^a$ is selected from hydrogen, substituted or unsubstituted alkyl, aryl, (heterocycloalkyl)-alkyl, heteroaralkyl, and aralkyl;
$R^b$ and $R^c$ are each independently selected from H, —OH, substituted or unsubstituted alkyl, —S(O)$_2$(alkyl), —S(O)$_2$(aryl), (heterocycloalkyl)alkyl, and heteroaralkyl;
(A) $R^2$ is selected from substituted or unsubstituted alkyl, alkenyl, alkynyl, aryl, cycloalkyl, aralkyl, heteroaralkyl, heteroaryl, heterocycloalkyl, (heterocycloalkyl)alkyl, (heteroaryl)heterocycloalkylene, (aryl)heterocycloalkylene, (aralkyl)heterocycloalkylene, (heteroaralkyl)heterocycloalkylene, ((heterocycloalkyl)alkyl)heterocycloalkylene, and —(CH$_2$)$_m$—(X)$_u$—(CH$_2$)$_n$—(Y)$_v$—$R^f$;
wherein
u and v are each independently 0 or 1, and u+v≠1;
m and n are each independently 0, 1, 2, 3, 4, 5, or 6, wherein m+n≥1;
X and Y are independently selected from —NH, —O— and —S—;
$R^f$ is selected from H, hydroxyl, substituted or unsubstituted alkyl and aryl; and
$R^5$ is selected from substituted or unsubstituted alkyl or alkyl-C(O)—; or
(B) $R^2$ is (heterocycloalkyl)alkyl; and
$R^5$ is selected from H, substituted or unsubstituted alkyl, and alkyl-C(O)—;
$R^3$ and $R^4$ are each independently selected from hydrogen, substituted or unsubstituted alkyl, and C(O)—R',
or $R^3$ and $R^4$ together with the boron atom to which they are bound form a 5- or 6-membered ring that is fully or partially saturated, and that optionally contains 1-3 additional heteroatom ring members selected from O, S, and N;
D is selected from substituted or unsubstituted alkylene, alkenylene, alkynylene, arylene, and cycloalkylene,
wherein one or more —CH$_2$— groups in D are optionally and independently replaced with a moiety Q that is selected from O, NR', S, SO, SO$_2$, and CR'R"; or
wherein any two adjacent —CH$_2$— groups optionally are replaced by two members of a cycloalkylenyl group;
provided that D does not contain two adjacent Q moieties selected from O, NR', S, SO, and SO$_2$; and
R' and R" are each independently selected from H, substituted or unsubstituted alkyl, and aryl;
wherein any alkyl, alkenyl, alkynyl, aryl, heteroaryl, cycloalkyl, or heterocycloalkyl is optionally further substituted;
or a pharmaceutically acceptable salt, stereoisomer, tautomer, or prodrug thereof.

In certain embodiments, the arginase inhibitor has the structure of the compound of Formula II, wherein:

$R^1$ is selected from the group consisting of —OH, $OR^a$, and $NR^bR^c$;

$R^a$ is selected from hydrogen, straight or branched chain $(C_1\text{-}C_6)$alkyl, $(C_3\text{-}C_{14})$aryl, $(C_3\text{-}C_{14})$heterocycloalkyl-$(C_1\text{-}C_6)$alkylene-, $(C_3\text{-}C_{14})$heteroaryl-$(C_1\text{-}C_6)$alkylene-, and $(C_3\text{-}C_{14})$aryl$(C_1\text{-}C_6)$alkylene-;

$R^b$ and $R^c$ are each independently selected from H, —OH, straight or branched $(C_1\text{-}C_6)$alkyl, —$S(O)_2$—$(C_1\text{-}C_6)$alkyl, $(C_3\text{-}C_{14})$aryl-$S(O)_2$—, $(C_3\text{-}C_{14})$heterocycloalkyl-$(C_1\text{-}C_6)$alkylene-, and $(C_3\text{-}C_{14})$heteroaryl-$(C_1\text{-}C_6)$alkylene-;

(A) $R^2$ is selected from straight or branched $(C_1\text{-}C_6)$alkyl, straight or branched $(C_2\text{-}C_6)$alkenyl, straight or branched $(C_2\text{-}C_6)$alkynyl, $(C_3\text{-}C_{14})$aryl, $(C_3\text{-}C_{14})$-cycloalkyl, $(C_3\text{-}C_{14})$aryl$(C_1\text{-}C_6)$alkylene-, $(C_3\text{-}C_{14})$heteroaryl-$(C_1\text{-}C_6)$alkylene-, $(C_3\text{-}C_{14})$heteroaryl, $(C_3\text{-}C_{14})$heterocycloalkyl, $(C_3\text{-}C_{14})$heterocycloalkyl-$(C_1\text{-}C_6)$alkylene-, $(C_3\text{-}C_{14})$heteroaryl-$(C_3\text{-}C_6)$heterocycloalkylene-, $(C_3\text{-}C_{14})$aryl-$(C_3\text{-}C_{14})$heterocycloalkylene-, $(C_3\text{-}C_{14})$-aryl-$(C_1\text{-}C_6)$alkyl-$(C_3\text{-}C_{14})$heterocycloalkylene-, $(C_3\text{-}C_{14})$heteroaryl-$(C_1\text{-}C_6)$alkyl-$(C_3\text{-}C_{14})$heterocycloalkylene-, $(C_3\text{-}C_{14})$heterocycloalkyl-$(C_1\text{-}C_6)$alkyl-$(C_3\text{-}C_{14})$heterocycloalkylene-, and —$(CH_2)_n$—$(X)_u$—$(CH_2)_n$—$(Y)_v$—$R^f$; wherein u and v are each independently 0 or 1, and u+v≤1;

m and n are each independently 0, 1, 2, 3, 4, 5, or 6, wherein m+n≥1;

X and Y are independently selected from —NH, —O— and —S—;

$R^f$ is selected from H, hydroxyl, straight or branched $(C_1\text{-}C_6)$alkyl and $(C_3\text{-}C_{14})$aryl; and $R^5$ is selected from straight or branched $(C_1\text{-}C_6)$ alkyl or $(C_1\text{-}C_6)$alkyl-C(O)—; or (B) $R^2$ is $(C_3\text{-}C_{14})$heterocycloalkyl-$(C_1\text{-}C_2)$alkylene-; and $R^5$ is selected from H, straight or branched $(C_1\text{-}C_6)$ alkyl, and $(C_1\text{-}C_6)$alkyl-C(O)—;

$R^3$ and $R^4$ are each independently selected from hydrogen, straight or branched $(C_1\text{-}C_6)$alkyl, and C(O)—R', or $R^3$ and $R^4$ together with the boron atom to which they are bound form a 5- or 6-membered ring that is fully or partially saturated, and that optionally contains 1-3 additional heteroatom ring members selected from O, S, and N;

D is selected from straight or branched $(C_1\text{-}C_6)$alkylene, straight or branched $(C_2\text{-}C_8)$alkenylene, straight or branched $(C_2\text{-}C_8)$alkynylene, $(C_3\text{-}C_{14})$arylene, and $(C_3\text{-}C_{14})$cycloalkylene, wherein one or more —$CH_2$— groups in D are optionally and independently replaced with a moiety Q that is selected from O, NR', S, SO, $SO_2$, and CR'R''; or wherein any two adjacent —$CH_2$— groups optionally are replaced by two members of a $(C_3\text{-}C_{14})$-cycloalkylenyl group;

provided that D does not contain two adjacent Q moieties selected from O, NR', S, SO, and $SO_2$;

wherein any alkyl, alkylene, alkenyl, alkenylene, alkynyl, or alkynylene is optionally substituted with one or more members selected from halogen, oxo, —COOH, —CN, —$NO_2$, —OH, —$NR^dR^e$, —$NR^gS(O)_2R^h$, $(C_1\text{-}C_6)$alkoxy, and $(C_3\text{-}C_{14})$aryloxy;

wherein $R^d$, $R^e$, $R^g$, and $R^h$ are each independently selected from H, straight or branched $(C_1\text{-}C_6)$alkyl, optionally substituted $(C_3\text{-}C_{14})$aryl$(C_1\text{-}C_6)$alkylene-, $(C_1\text{-}C_6)$alkoxy, optionally substituted $(C_3\text{-}C_{14})$aryl, $(C_1\text{-}C_6)$hydroxyalkyl, $(C_1\text{-}C_6)$aminoalkyl, $H_2N(C_1\text{-}C_6)$alkylene-, optionally substituted $(C_3\text{-}C_6)$cycloalkyl, optionally substituted $(C_3\text{-}C_{14})$heterocycloalkyl, optionally substituted $(C_3\text{-}C_{14})$heteroaryl, optionally substituted $(C_3\text{-}C_{14})$aryl-$(C_1\text{-}C_6)$alkylene-, NR'R''C(O)—, and $(C_3\text{-}C_6)$aryl-$(C_3\text{-}C_{14})$-cycloalkylene-, and R' and R'' are each independently selected from H, $(C_1\text{-}C_8)$alkyl, and $(C_3\text{-}C_6)$aryl; and wherein any aryl, heteroaryl, cycloalkyl, or heterocycloalkyl is optionally substituted with one or more members selected from halogen, —OH, oxo, —COOH, $(C_3\text{-}C_{14})$aryl$(C_1\text{-}C_6)$alkylene-, —CN, —$NO_2$, —$NH_2$, $(C_1\text{-}C_6)$alkyl-S—, $(C_3\text{-}C_{14})$cycloalkyl, $(C_3\text{-}C_{14})$heterocycloalkyl, $(C_3\text{-}C_{14})$aryl, $(C_3\text{-}C_{14})$heteroaryl, —C(O)NH—$(C_1\text{-}C_6)$alkyl, —NHC(O)—$(C_1\text{-}C_6)$alkyl, $(C_1\text{-}C_6)$alkyl, $(C_2\text{-}C_8)$alkenyl, $(C_2\text{-}C_8)$alkynyl, $(C_1\text{-}C_6)$alkoxy, $(C_1\text{-}C_6)$haloalkyl, and $(C_1\text{-}C_6)$hydroxyalkyl.

In certain embodiments, D is selected from:
-$L^1$-$L^2$-$CH_2$—$CH_2$—,
—$CH_2$-$L^1$-$L^2$-$CH_2$—
$CH_2$—$CH_2$-$L^1$-$L^2$,
-$L^1$-$CH_2$—$CH_2$-$L^2$-, and
-$L^1$-$CH_2$-$L^2$-$CH_2$, and wherein $L^1$ and $L^2$ are independently selected from O, NR', S, SO, $SO_2$, and CR'R''.

In certain embodiments, D is straight or branched $(C_3\text{-}C_5)$alkylene. In certain preferred embodiments, D is butylene.

In certain embodiments, $R^1$ is —OH.

In certain embodiments, (A) $R^2$ is selected from straight or branched $(C_1\text{-}C_6)$alkyl, straight or branched $(C_2\text{-}C_6)$alkenyl, straight or branched $(C_2\text{-}C_6)$alkynyl, $(C_3\text{-}C_{14})$aryl, $(C_3\text{-}C_{14})$-cycloalkyl, $(C_3\text{-}C_{14})$aryl$(C_1\text{-}C_6)$alkylene-, $(C_3\text{-}C_{14})$heteroaryl-$(C_1\text{-}C_6)$alkylene-, $(C_3\text{-}C_{14})$heteroaryl, $(C_3\text{-}C_{14})$heterocycloalkyl, $(C_3\text{-}C_{14})$heterocycloalkyl-$(C_1\text{-}C_6)$alkylene-, $(C_3\text{-}C_{14})$heteroaryl-$(C_3\text{-}C_6)$heterocycloalkylene-, $(C_3\text{-}C_{14})$aryl-$(C_3\text{-}C_{14})$heterocycloalkylene-, $(C_3\text{-}C_{14})$-aryl-$(C_1\text{-}C_6)$alkyl-$(C_3\text{-}C_{14})$heterocycloalkylene-, $(C_3\text{-}C_{14})$heteroaryl-$(C_1\text{-}C_6)$alkyl-$(C_3\text{-}C_{14})$heterocycloalkylene-, $(C_3\text{-}C_{14})$heterocycloalkyl-$(C_1\text{-}C_6)$alkyl-$(C_3\text{-}C_{14})$heterocycloalkylene-, and —$(CH_2)_n$—$(X)_n$—$(CH_2)_n$—$(Y)_v$—$R^f$; and each of $R^3$ and $R^4$ is hydrogen

OR (B) $R^2$ is $(C_3\text{-}C_{14})$heterocycloalkyl-$(C_1\text{-}C_2)$alkylene-; and each of $R^3$, and $R^4$ and $R^5$ is hydrogen.

In certain embodiments, $R^2$ is selected from $(C_1\text{-}C_6)$alkyl, $(C_3\text{-}C_{14})$aryl, $(C_3\text{-}C_{14})$heteroaryl, $(C_3\text{-}C_{14})$heterocycloalkyl, $(C_3\text{-}C_{14})$heterocycloalkyl-$(C_1\text{-}C_6)$alkylene-, $(C_3\text{-}C_{14})$heteroaryl-$(C_1\text{-}C_6)$alkylene-, $(C_3\text{-}C_{14})$aryl-$(C_1\text{-}C_6)$alkylene- and —$(CH_2)_n$—$(X)_u$—$(CH_2)_m$—$(Y)_v$—$R^f$, and $R^5$ is selected from straight or branched $(C_1\text{-}C_6)$ alkyl or $(C_1\text{-}C_6)$alkyl-C(O)—.

In certain embodiments, $R^2$ is alkyl optionally substituted by hydroxy or —$NR^dR^e$. In certain such embodiments, $R^d$ and $R^e$ is independently selected from H, straight or branched $(C_1\text{-}C_6)$alkyl, $(C_1\text{-}C_6)$aminoalkyl, optionally substituted $(C_3\text{-}C_{14})$aryl-$(C_1\text{-}C_6)$alkylene-, optionally substituted $(C_3\text{-}C_{14})$aryl, and optionally substituted $(C_3\text{-}C_6)$cycloalkyl. In certain preferred embodiments, $R^d$ and $R^e$ is $(C_1\text{-}C_6)$aminoalkyl.

In certain embodiments, $R^2$ is —$(CH_2)_n$—$(X)_u$—$(CH_2)_n$—$(Y)_v$—$R^f$. In certain such embodiments, X and Y are each independently —NH—. In further certain such embodiments, m is 1 and n is 2. In further certain such embodiments, each of u and v is 1.

In certain embodiments, $R^2$ is $(C_3$-$C_6)$heterocycloalkyl-$(C_1$-$C_2)$alkylene optionally substituted with one or more members selected from —$(C_1$-$C_6)$alkoxy, —$(C_1$-$C_6)$alkyl, and —OH.

In certain embodiments, $R^2$ is $(C_3$-$C_{14})$heteroaryl-$(C_1$-$C_6)$alkylene-.

In certain embodiments, the arginase inhibitor of formula II is not 2-amino-4-borono-2-methylbutanoic acid.

In certain exemplary embodiments, the arginase inhibitor is selected from the following compounds:

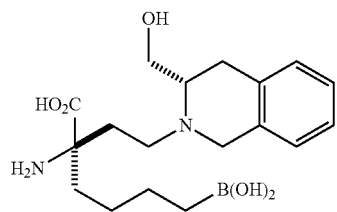
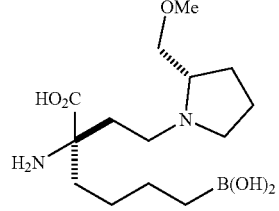
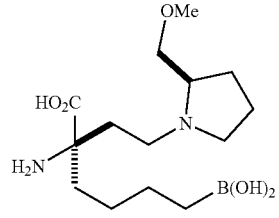
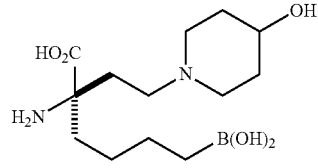
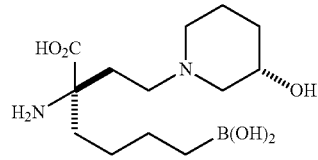
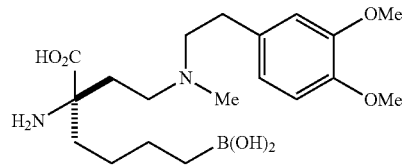
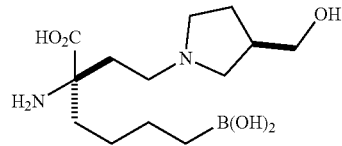

-continued

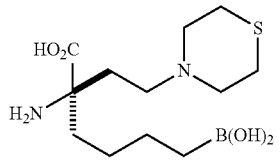
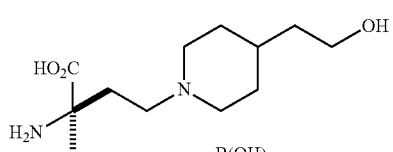
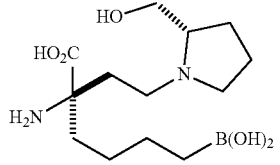
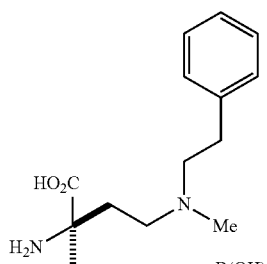
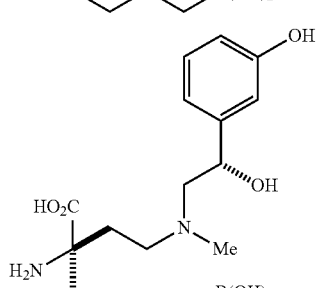
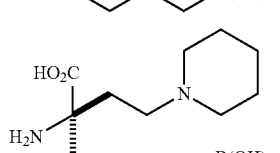
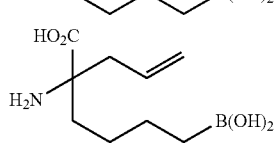
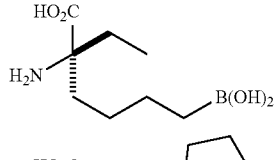
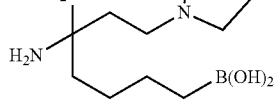

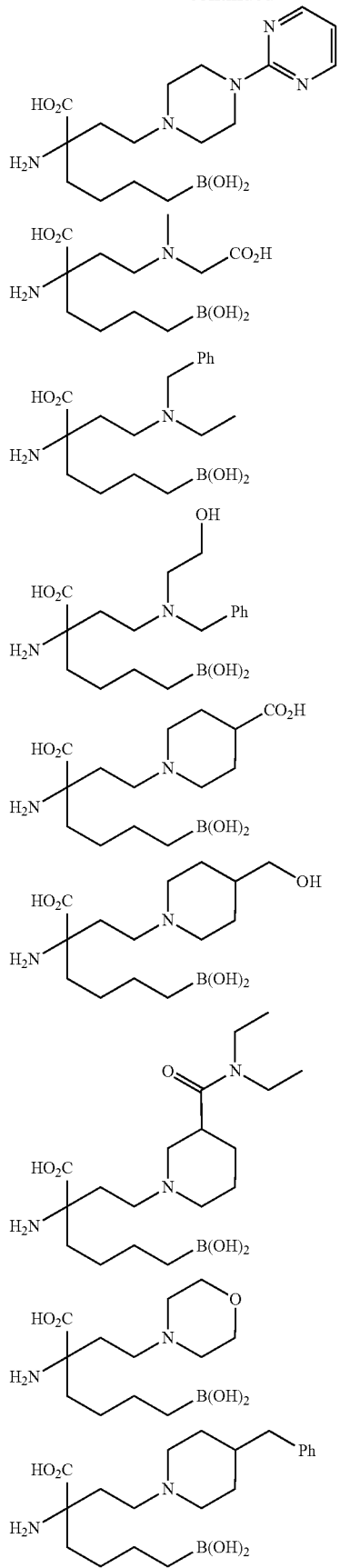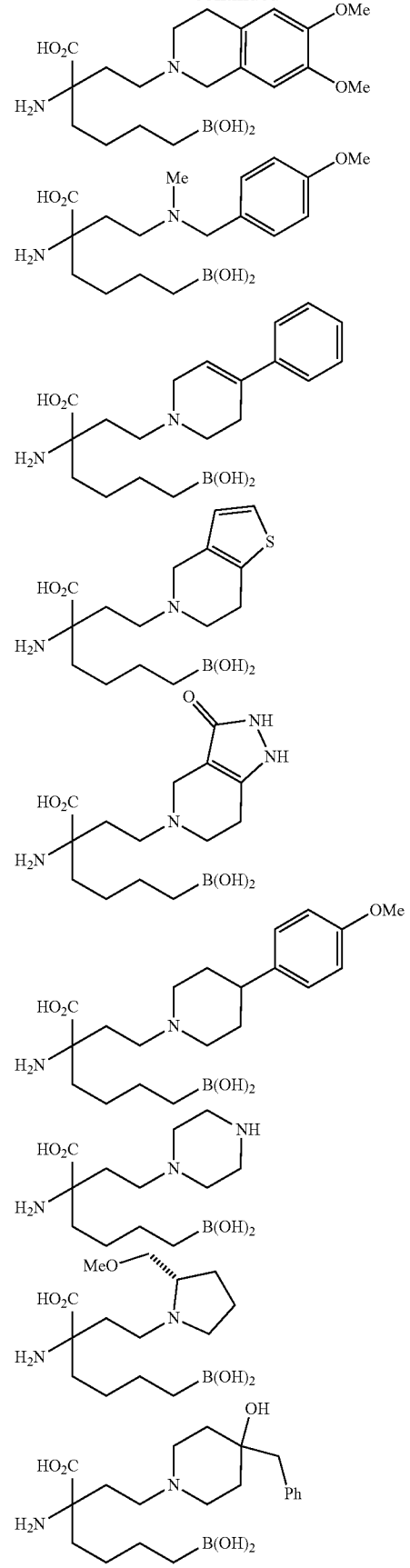

-continued
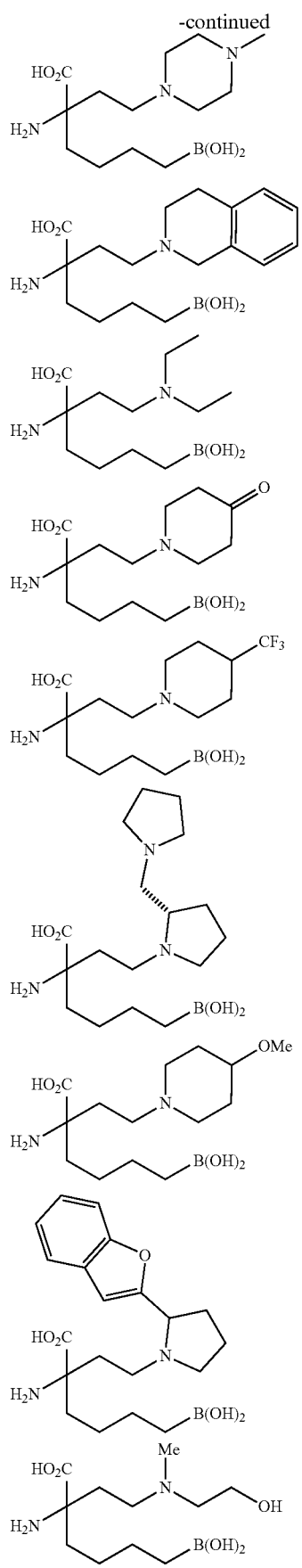
-continued
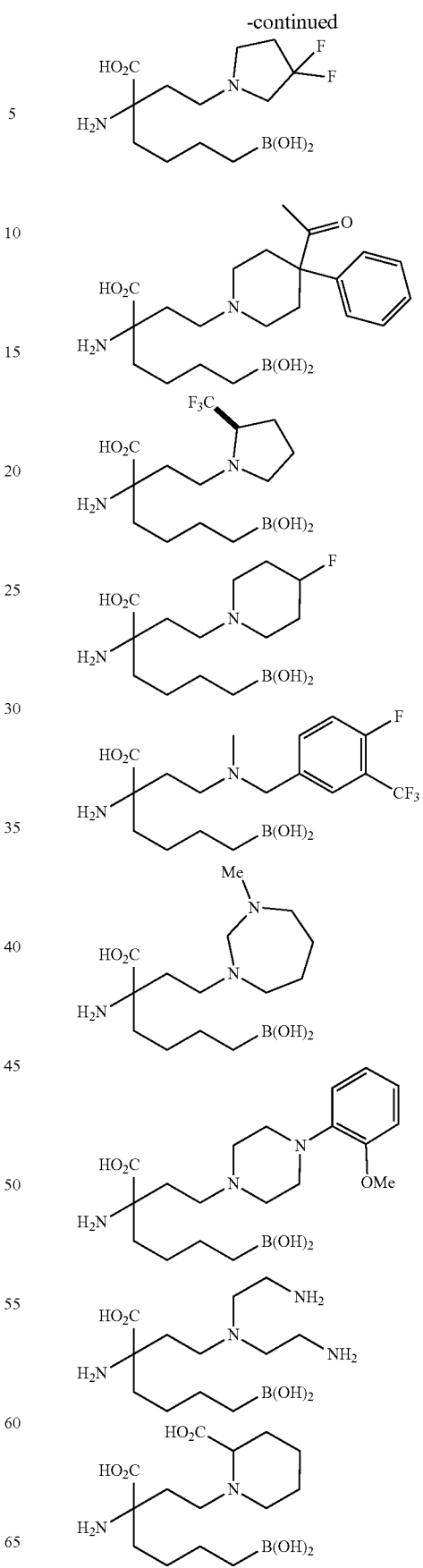

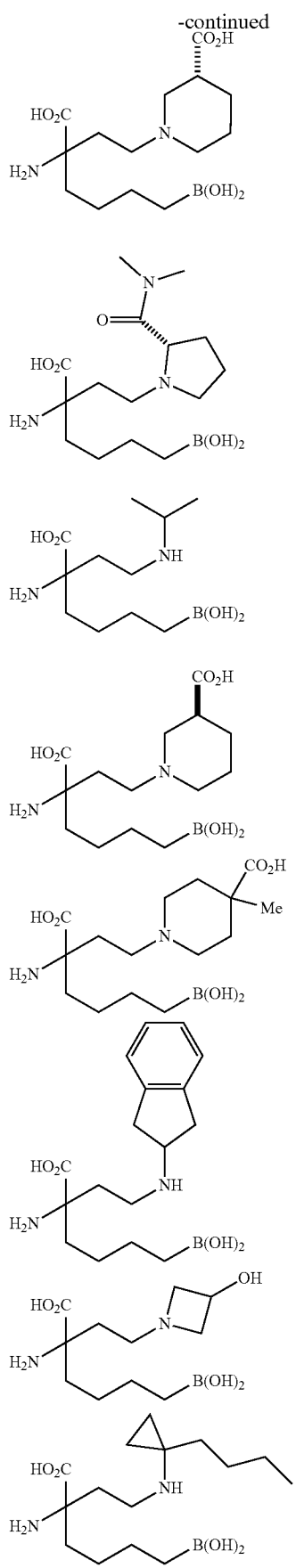
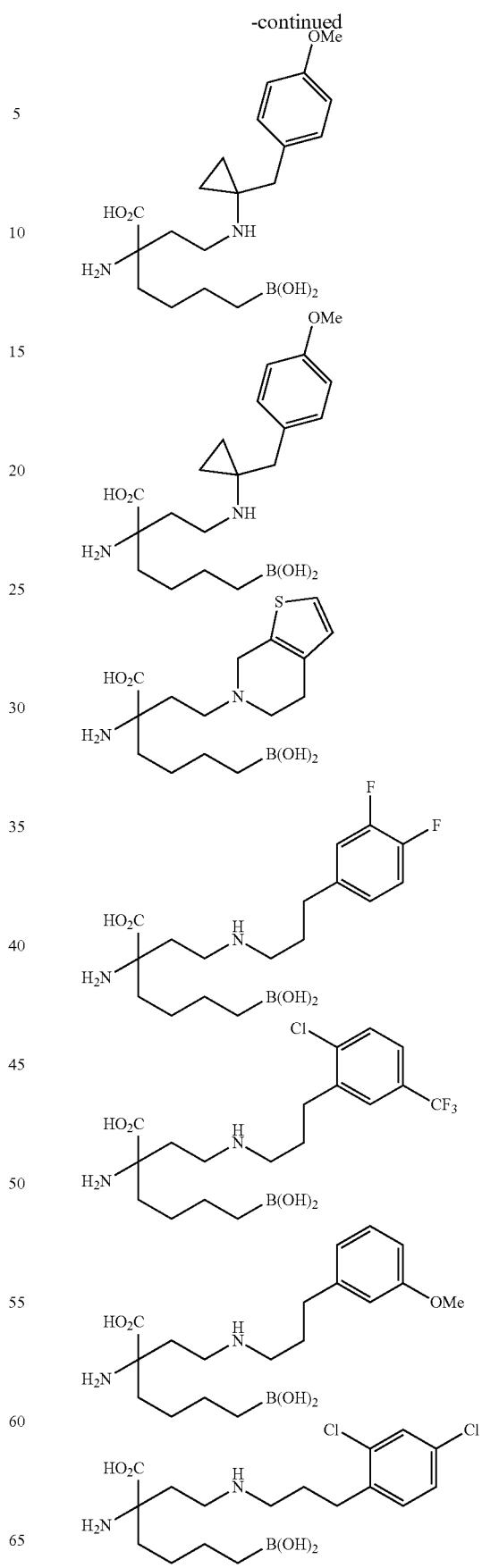

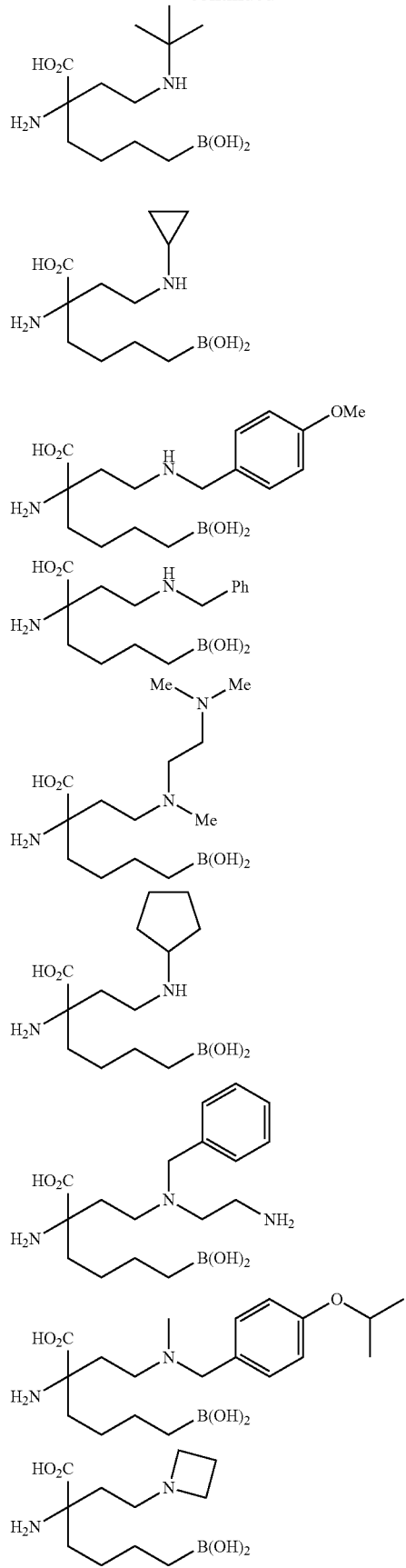
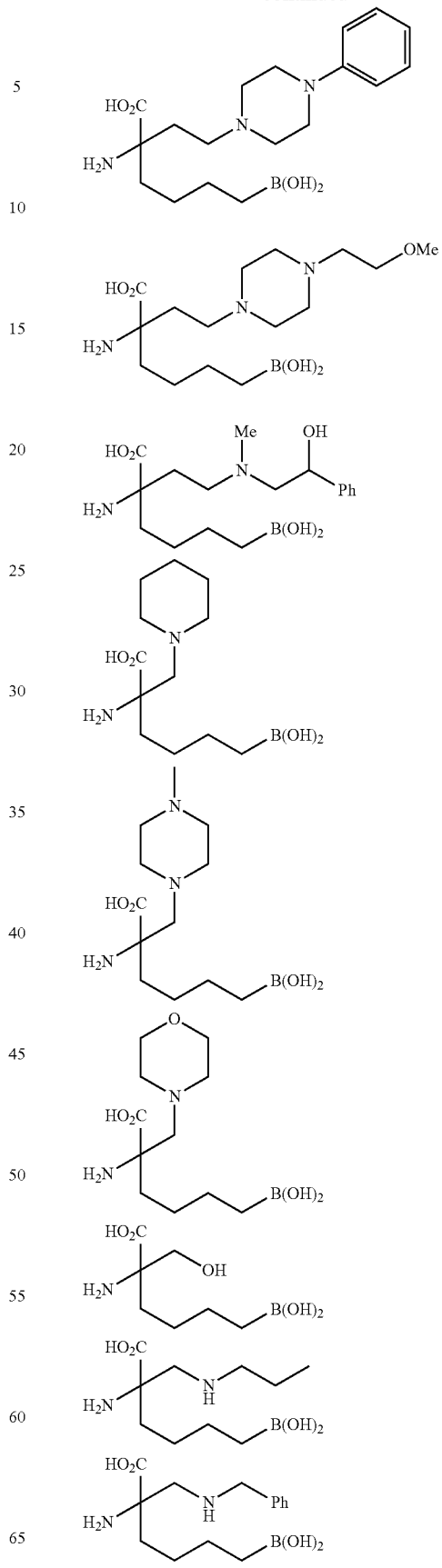

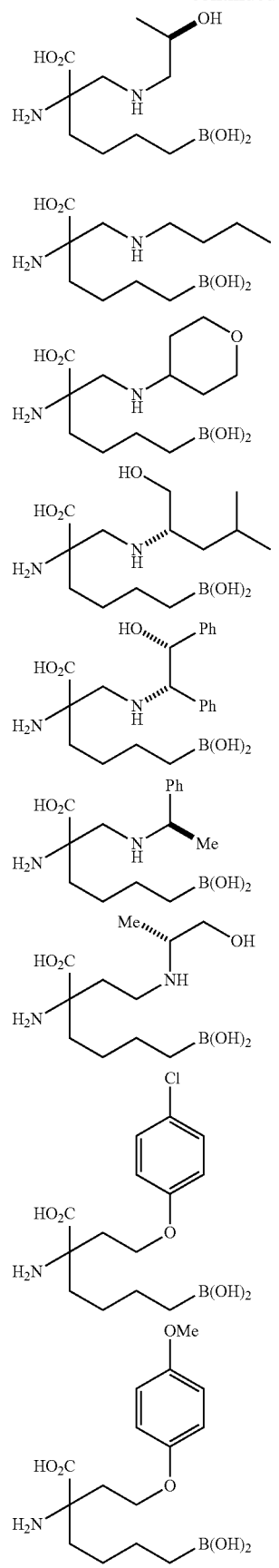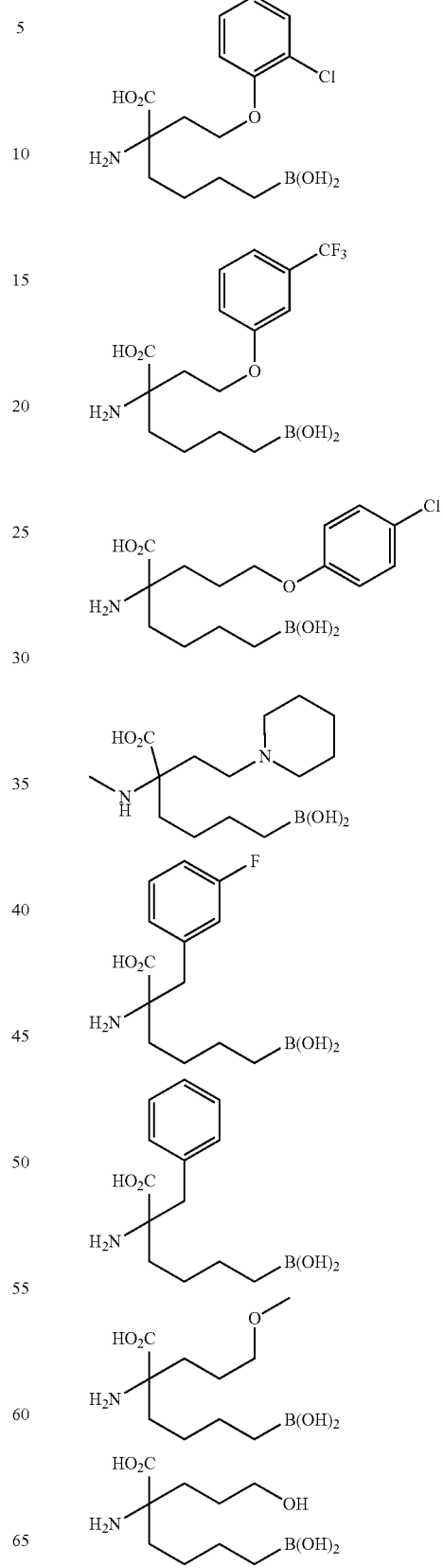

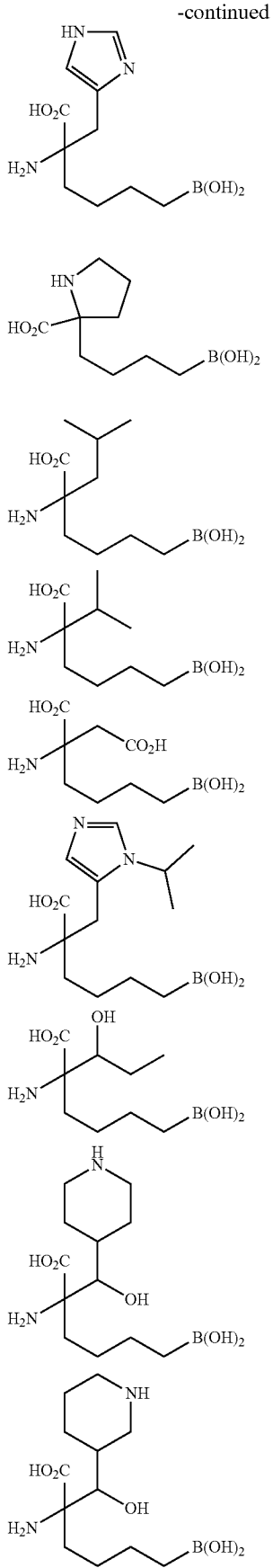
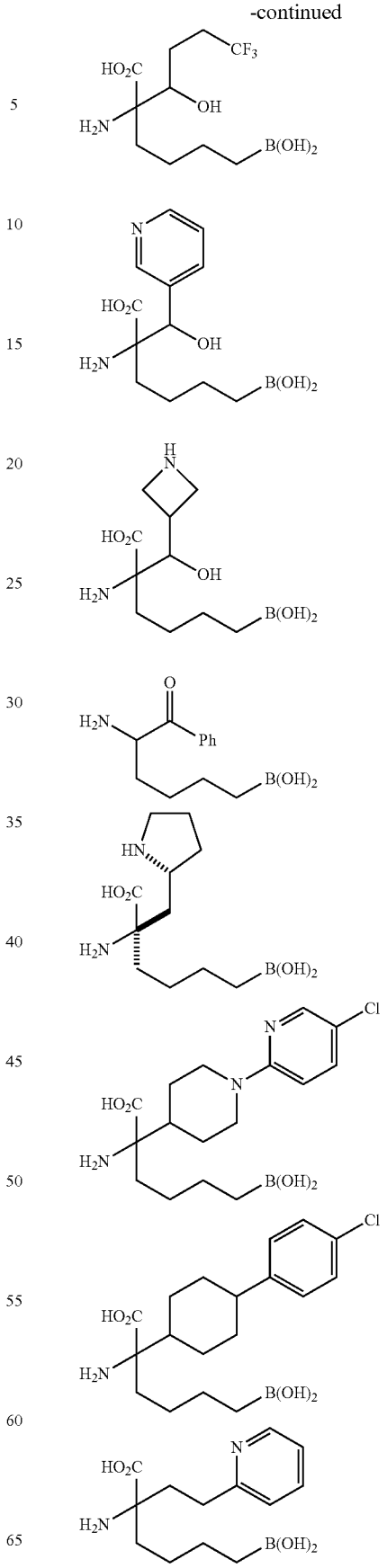

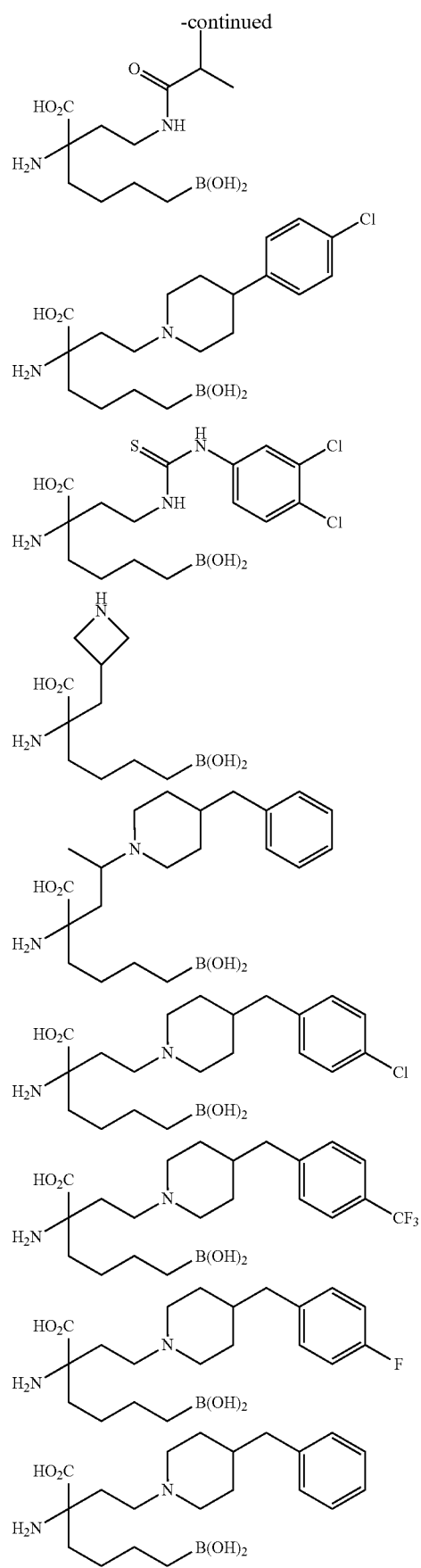
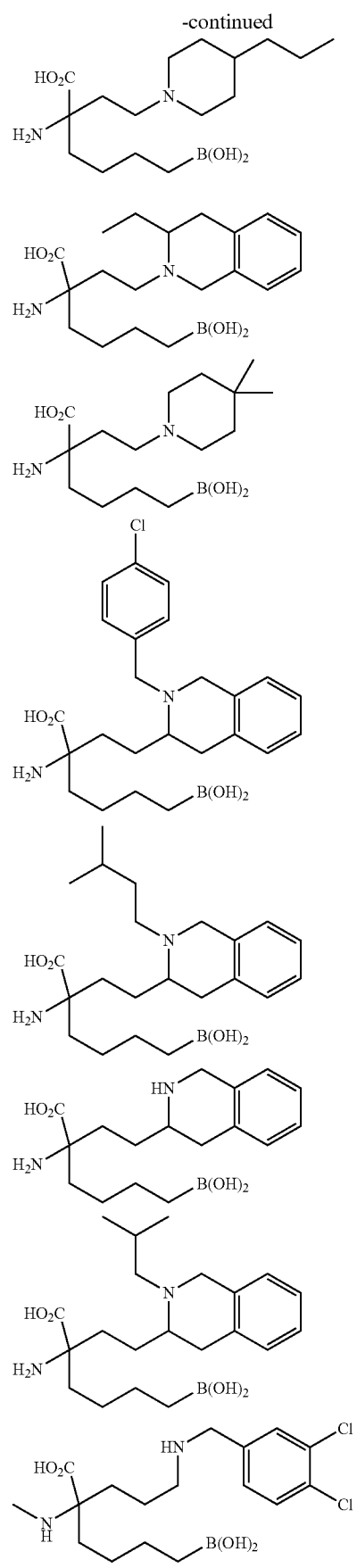

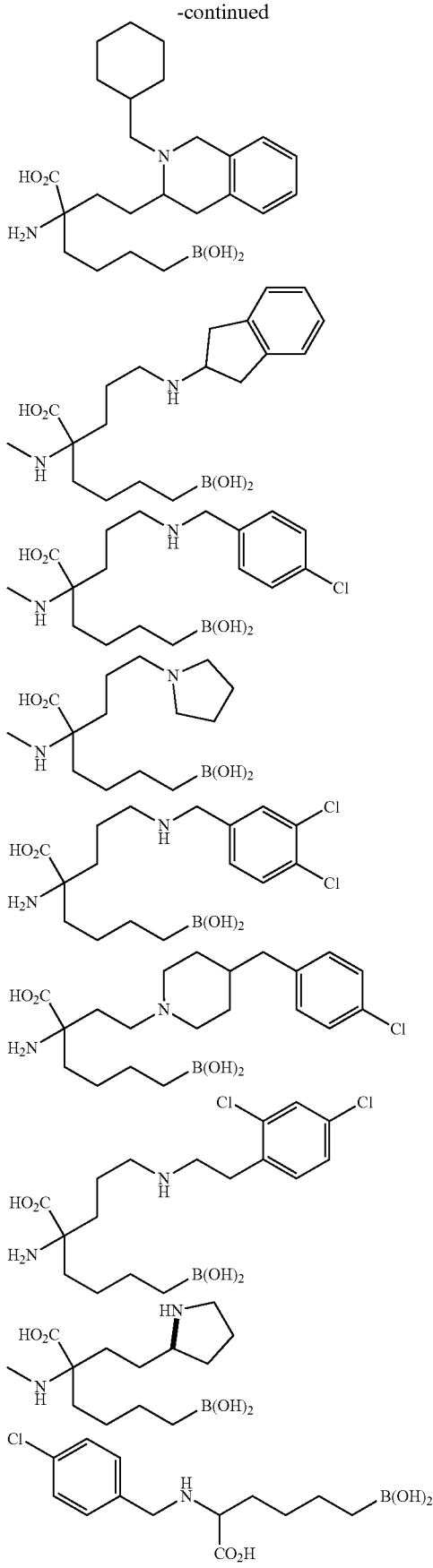

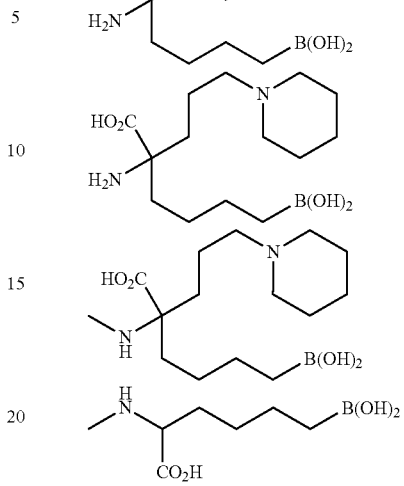

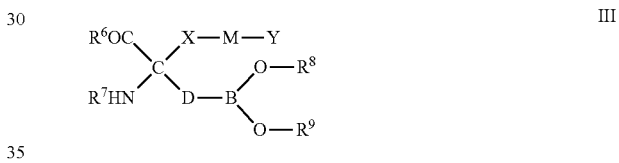

In certain embodiments, the arginase inhibitor used in the methods of the invention is a compound having the structure of Formula III, $$\underset{R^7HN}{\overset{R^6OC}{>}}C\underset{D}{\overset{X-M-Y}{<}}B\underset{O-R^9}{\overset{O-R^8}{<}} \quad III$$

wherein
R$^6$ is selected from OR$^a$, and NR$^b$R$^c$;
  R$^a$ is selected from hydrogen, substituted or unsubstituted alkyl, cycloalkyl, aryl, (heterocycloalkyl)alkyl, heteroaralkyl, and aralkyl;
  R$^b$ and R$^c$ are each independently selected from H, —OH, substituted or unsubstituted alkyl, —S(O)$_2$(alkyl), —S(O)$_2$(aryl), (heterocycloalkyl)alkyl, and heteroaralkyl;
R$^7$ is selected from H, substituted or unsubstituted alkyl, aralkyl, heteroaralkyl, (heterocycloalkyl)alkyl and (alkyl)C(O)—;
X is selected from cycloalkylene and heterocycloalkylene,
Y is selected from H, alkyl, —NR'R", hydroxyalkyl, cycloalkyl, (cycloalkyl)alkyl, aryl, aralkyl, heterocycloalkyl, (heterocycloalkyl)alkyl, heteroaryl, heteroaralkyl, (heteroaryl)heterocycloalkyl, (aryl)heterocycloalkyl, (aralkyl)heterocycloalkyl, (heteroaralkyl)heterocycloalkyl, and ((heterocycloalkyl)alkyl)heterocycloalkyl;
M is selected from a bond, alkylene, —O—, —C(O)—, —C(S)—, —C(O)NH—, —C(S)NH—, —S—, —S(O)—, —S(O)$_2$—, —NR'—, and —C=NR$^{11}$—;
R$^8$ and R$^9$ are independently selected from hydrogen, substituted or unsubstituted alkyl, cycloalkyl, aryl, and C(O)—R',
or R$^8$ and R$^9$ together with the boron atom to which they are bound form a 5- or 6-membered ring that is fully saturated or partially saturated and that optionally contains 1-3 additional heteroatom ring members selected from O, S, and N, wherein the ring is optionally fused with a cycloalkyl, heterocyclic or aromatic ring;

D is selected from substituted or unsubstituted alkylene, alkenylene, alkynylene, arylene, and cycloalkylene,
  wherein one or more —CH$_2$— groups in D are optionally and independently replaced with a moiety Q that is selected from O, NR', S, SO, SO$_2$, and CR'R''; or
  wherein any two adjacent —CH$_2$— groups optionally are replaced by two members of a cycloalkylenyl group; and
  provided that D does not contain two adjacent Q moieties selected from O, NR', S, SO, and SO$_2$; and R' and R'' are independently selected from H, substituted or unsubstituted alkyl, —C(O)(alkyl), aryl, aralkyl, aminoalkyl, cycloalkyl, heterocycloalkyl, heteroaryl;
  wherein any alkyl, alkenyl, alkynyl, aryl, heteroaryl, cycloalkyl, or heterocycloalkyl is optionally further substituted;

or a pharmaceutically acceptable salt, stereoisomer, tautomer, or prodrug thereof.

In certain embodiments, the arginase inhibitor is a compound of Formula III,
wherein:
  $R^6$ is selected from $OR^a$, and $NR^bR^c$;
    $R^a$ is selected from hydrogen, straight or branched chain (C$_1$-C$_6$)alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl (C$_1$-C$_6$)alkylene-;
    $R^b$ and $R^c$ are each independently selected from H, —OH, straight or branched (C$_1$-C$_6$)alkyl, —S(O)$_2$—(C$_1$-C$_6$)alkyl, (C$_3$-C$_{14}$)aryl-S(O)$_2$—, (C$_3$-C$_{14}$)heterocycloalkyl-(C$_1$-C$_6$)alkylene-, and (C$_3$-C$_{14}$)heteroaryl-(C$_1$-C$_6$)alkylene-;
  $R^7$ is selected from H, straight or branched (C$_1$-C$_6$) alkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heterocycloalkyl-(C$_1$-C$_6$)alkylene- and (C$_1$-C$_6$)alkyl-C(O)—;
  X is selected from (C$_3$-C$_{14}$)-cycloalkylene and (C$_3$-C$_{14}$) heterocycloalkylene,
  Y is selected from H, —NR'R'', hydroxy(C$_1$-C$_6$)alkylene, (C$_3$-C$_{14}$)-cycloalkyl, (C$_3$-C$_{14}$)-cycloalkyl-(C$_1$-C$_6$)alkylene, (C$_3$-C$_{14}$)aryl, (C$_3$-C$_{14}$)aryl-(C$_1$-C$_6$)alkylene, (C$_3$-C$_{14}$)heterocycloalkyl, (C$_3$-C$_{14}$)heterocycloalkyl-(C$_1$-C$_6$)alkylene, (C$_3$-C$_{14}$)heteroaryl, (C$_3$-C$_{14}$)heteroaryl-(C$_1$-C$_6$)alkylene, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$—C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, and (C$_3$-C$_{14}$) heterocycloalkyl-(C$_1$-C$_6$)alkyl-(C$_3$-C$_{14}$) heterocycloalkylene-;
  M is selected from a bond, —(C$_1$-C$_6$)alkylene-, —O—, —C(O)—, —C(S)—, —C(O)NH—, —C(S)NH—, —S—, —S(O)—, —S(O)$_2$—, —NR'—, and —C=NR$^{11}$—;
  $R^8$ and $R^9$ are independently selected from hydrogen, straight or branched (C$_1$-C$_6$)alkyl, (C$_3$-C$_8$)cycloalkyl, (C$_3$-C$_{14}$)aryl, and C(O)—R',
  or $R^8$ and $R^9$ together with the boron atom to which they are bound form a 5- or 6-membered ring that is fully saturated, or partially saturated and that optionally contains 1-3 additional heteroatom ring members selected from O, S, and N,
    wherein the ring is optionally fused with a cycloalkyl, heterocyclic or aromatic ring;

D is selected from straight or branched (C$_3$-C$_5$)alkylene, straight or branched (C$_2$-C$_8$)alkenylene, straight or branched (C$_2$-C$_8$)alkynylene, (C$_3$-C$_{14}$)arylene, and (C$_3$-C$_{14}$)cycloalkylene,
    wherein one or more —CH$_2$— groups in D are optionally and independently replaced with a moiety Q that is selected from O, NR', S, SO, SO$_2$, and CR'R''; or
    wherein any two adjacent —CH$_2$— groups optionally are replaced by two members of a (C$_3$-C$_{14}$)-cycloalkylenyl group;
    provided that D does not contain two adjacent Q moieties selected from O, NR', S, SO, and SO$_2$; and
  R' and R'' are independently selected from H, (C$_1$-C$_8$) alkyl, —C(O)—(C$_1$-C$_8$)alkylene, optionally substituted (C$_3$-C$_6$)aryl, optionally substituted (C$_3$-C$_{14}$)aryl (C$_1$-C$_6$)alkylene-, optionally substituted (C$_1$-C$_6$) aminoalkyl, optionally substituted (C$_3$-C$_6$)cycloalkyl, optionally substituted (C$_3$-C$_{14}$)heterocycloalkyl, optionally substituted (C$_3$-C$_{14}$)heteroaryl;
    wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkyl, (C$_1$-C$_6$)haloalkyl, (C$_1$-C$_6$)haloalkoxy, (C$_1$-C$_6$)alkoxy, (C$_3$-C$_{14}$)aryl, (C$_3$-C$_{14}$)heteroaryl, (C$_3$-C$_{14}$)heterocycloalkyl, (C$_3$-C$_{14}$)heteroaryl-(C$_1$-C$_6$)alkylene and (C$_3$-C$_{14}$)aryloxy;
    wherein $R^d$, $R^e$, $R^g$, and $R^h$ are each independently selected from H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, and NR'R''C(O)—.

In certain embodiments of the compound of Formula III, D is selected from:
  -L$^1$-L$^2$-CH$_2$—CH$_2$—,
  —CH$_2$-L$^1$-L$^2$-CH$_2$—
  —CH$_2$—CH$_2$-L$^1$-L$^2$,
  -L$^1$-CH$_2$—CH$_2$-L$^2$-, and
  -L$^1$-CH$_2$-L$^2$-CH$_2$—,
wherein L$^1$ and L$^2$ are independently selected from O, NR', S, SO, SO$_2$, and CR'R''.

In certain embodiments, D is straight or branched (C$_3$-C$_5$)alkylene, such as butylene.

In certain embodiments, $R^1$ is —OH.

In certain embodiments, $R^7$, $R^8$ and $R^9$ are hydrogen.

In certain embodiments, X is (C$_3$-C$_{14}$)-cycloalkylene, M is selected from a bond, —(C$_1$-C$_6$)alkylene-, —O—, —C(O)—, —C(S)—, —C(O)NH—, —C(S)NH—, —S—, —S(O)—, —S(O)$_2$—, —NR'—, and —C=NR$^{11}$—; and Y is —NR'R''.

In certain embodiments, M is a bond and Y is —NH$_2$.

In certain embodiments, X is (C$_3$-C$_{14}$)heterocycloalkylene; M is selected from a bond, —(C$_1$-C$_6$)alkylene-, —O—, —C(O)—, —C(S)—, —C(O)NH—, —C(S)NH—, —S—, —S(O)—, —S(O)$_2$—, —NR'—, and —C=NR$^{11}$—; and Y is selected from (C$_3$-C$_{14}$)-cycloalkyl, (C$_3$-C$_{14}$)aryl, (C$_3$-C$_{14}$)aryl-(C$_1$-C$_6$)alkylene, (C$_3$-C$_{14}$)heteroaryl and (C$_3$-C$_{14}$)heteroaryl-(C$_1$-C$_6$)alkylene.

In certain embodiments, the arginase inhibitor used in the methods of the invention is selected from:

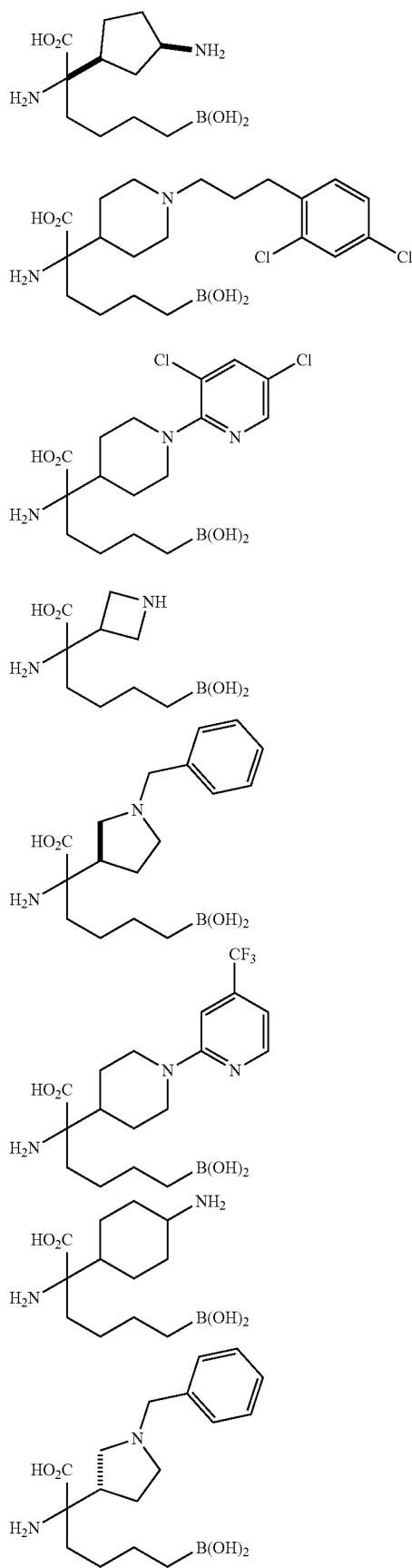
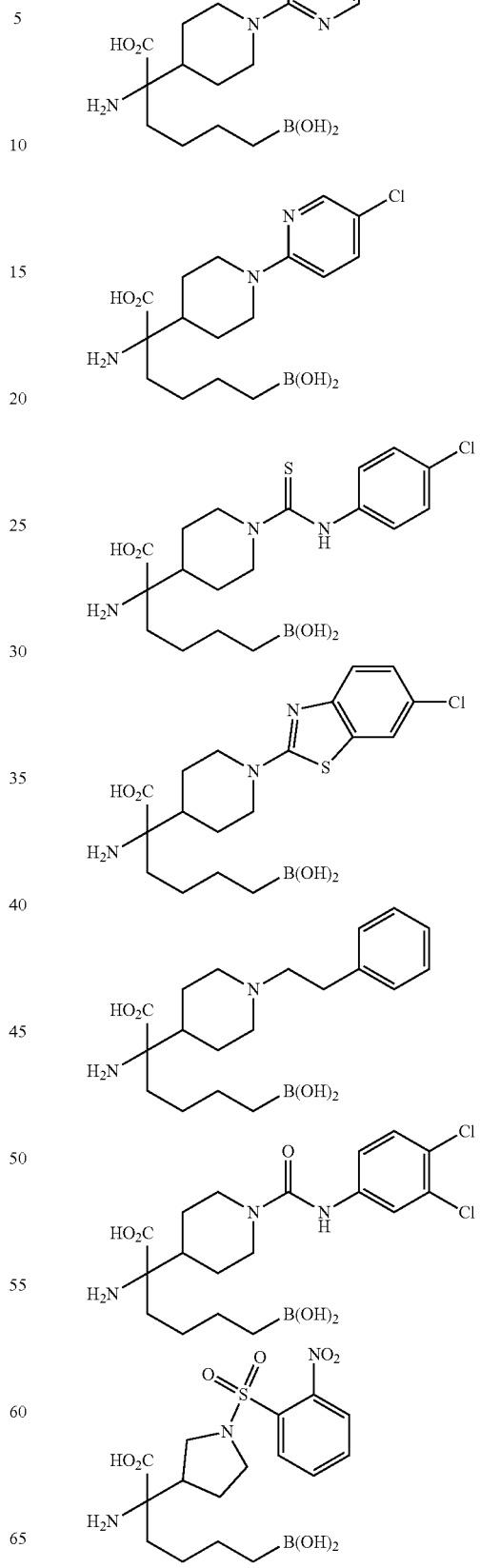

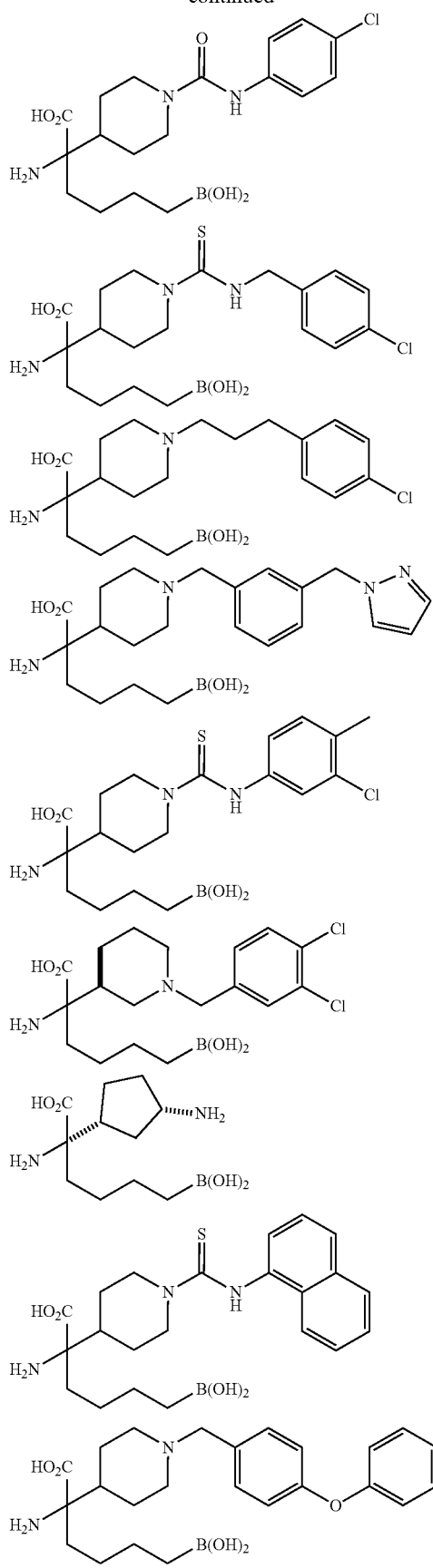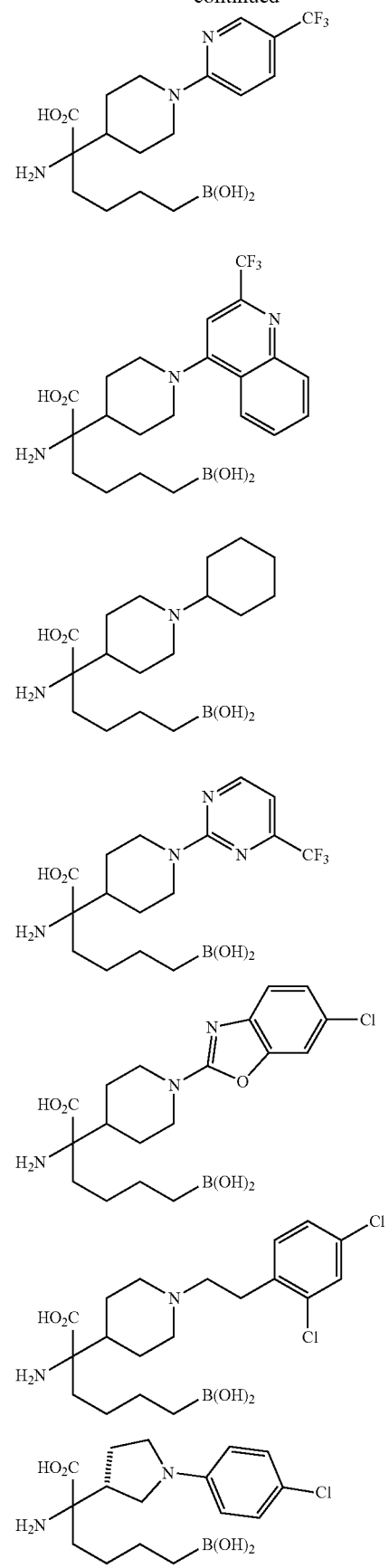

45
-continued
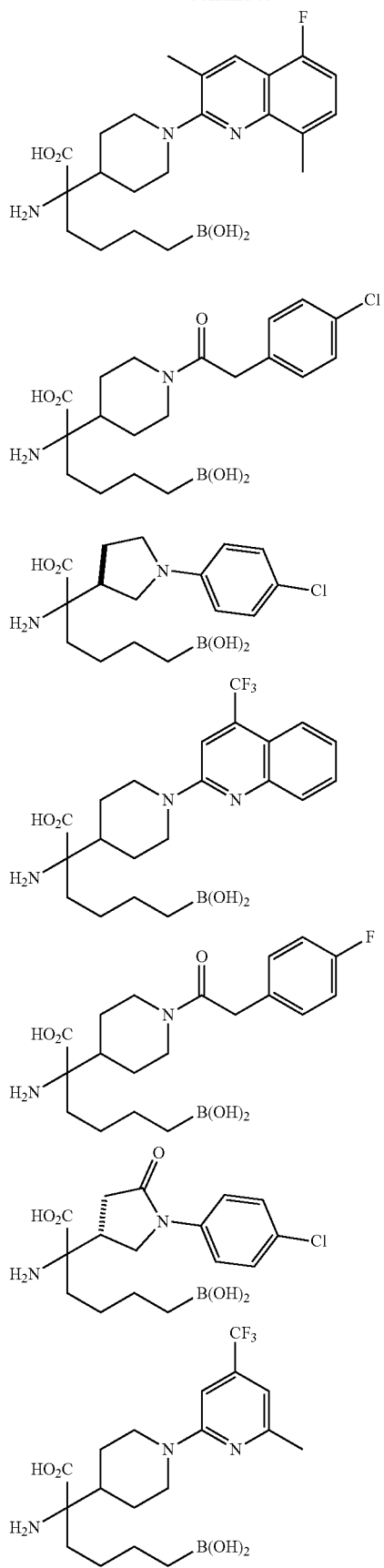
46
-continued
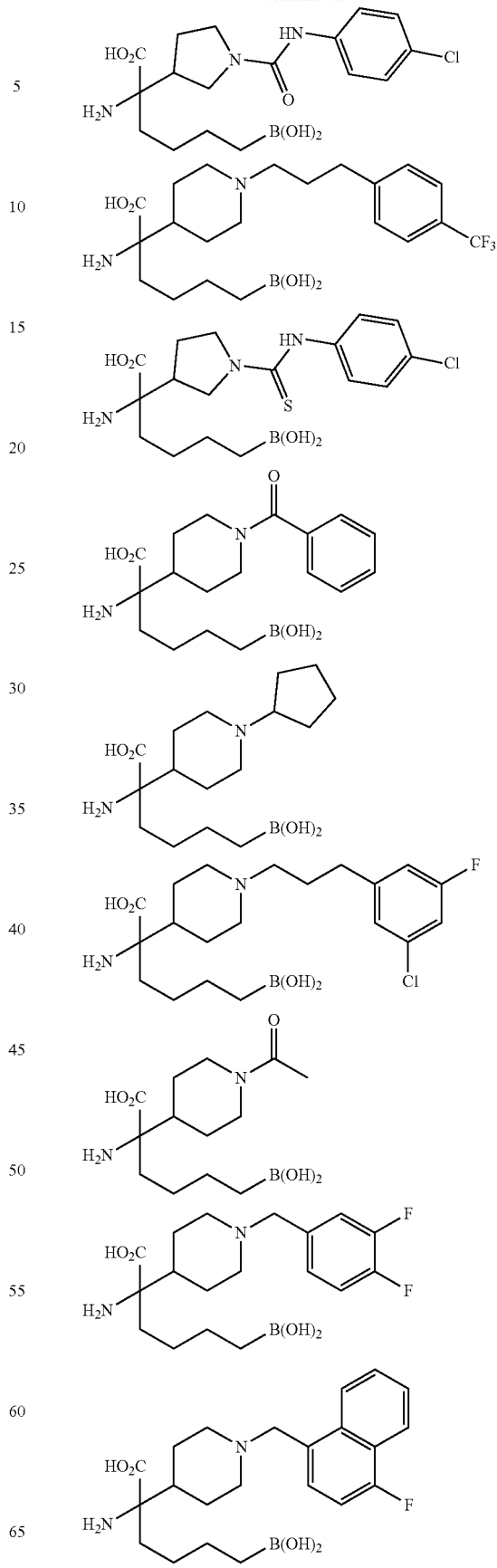

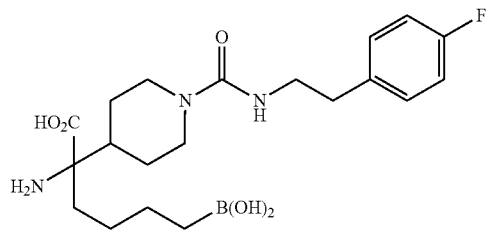
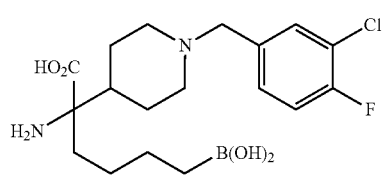
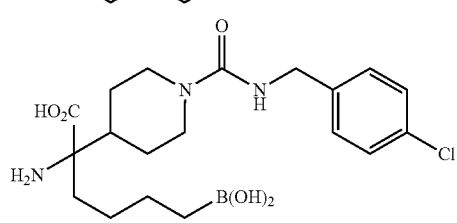
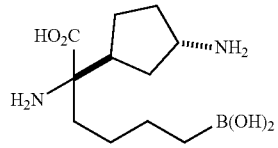
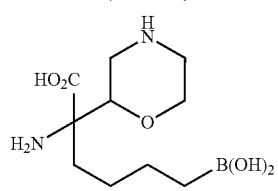
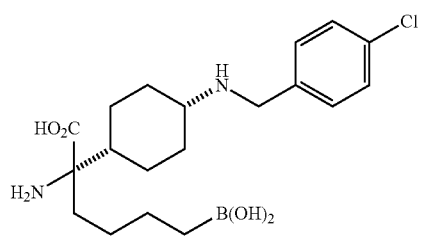
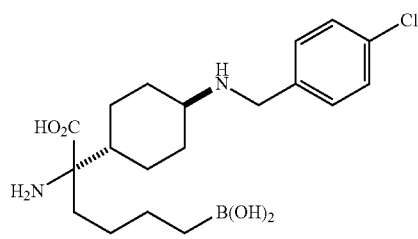
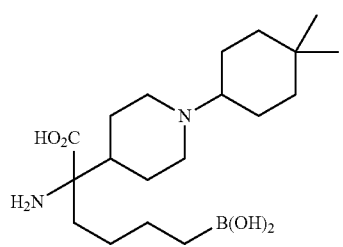
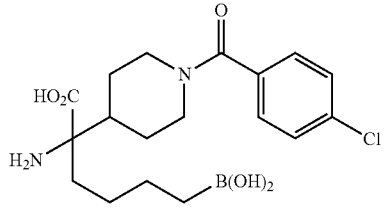
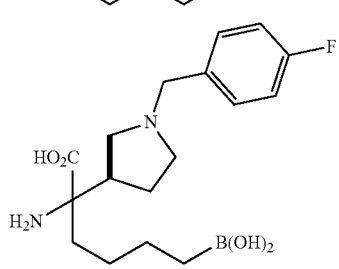
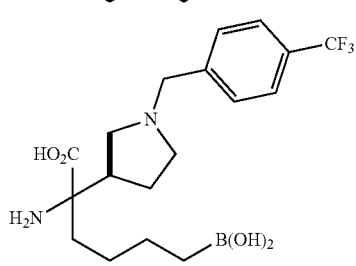
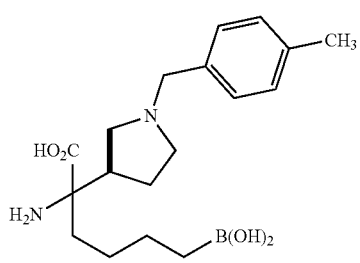
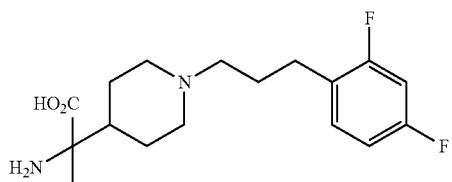
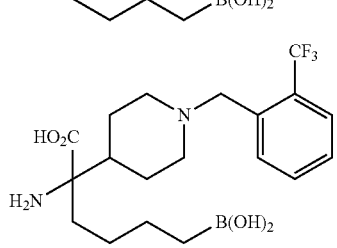
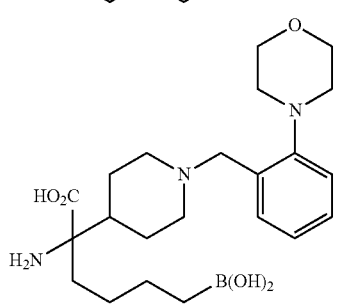

-continued
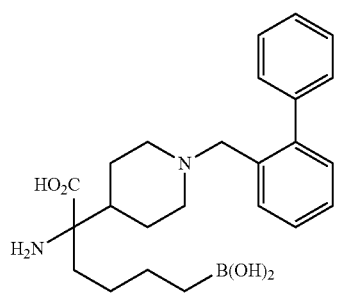
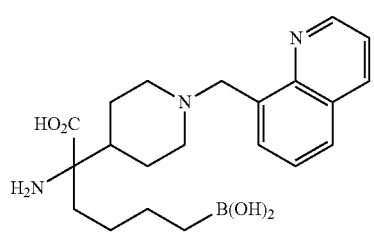
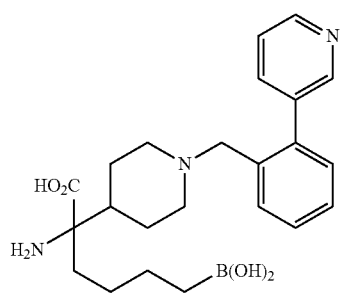
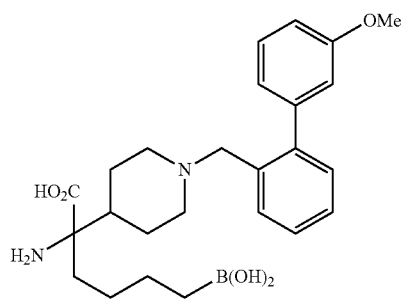
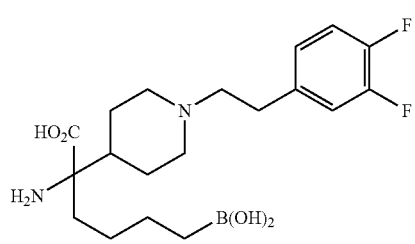
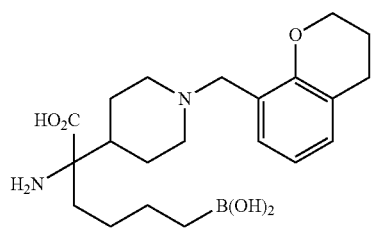
-continued
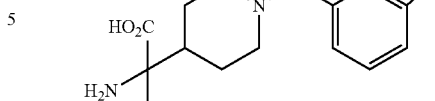
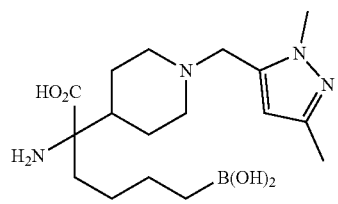
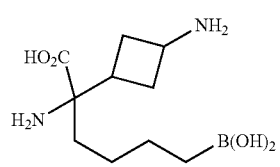
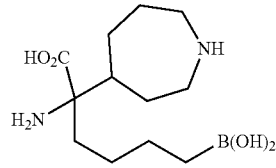
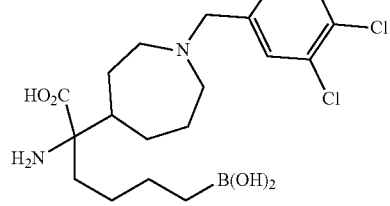
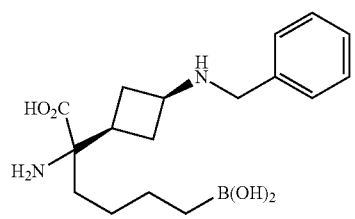
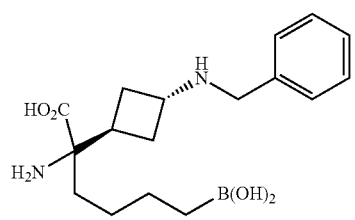
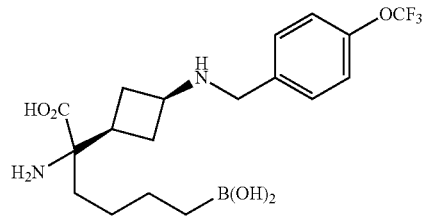

-continued
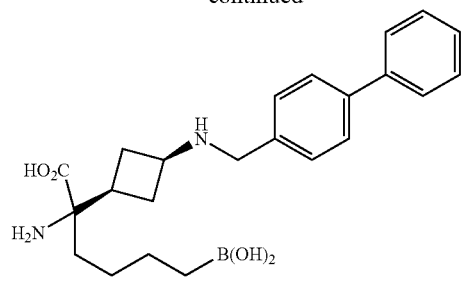
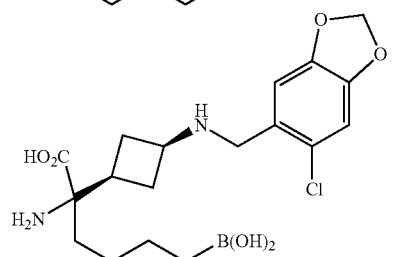
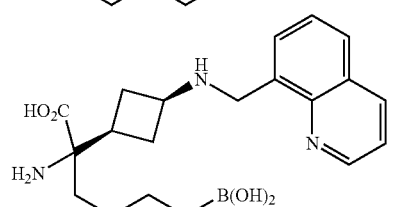
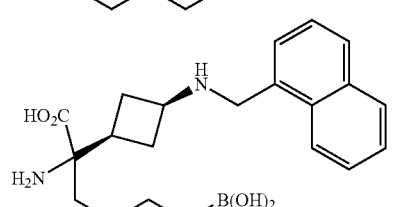
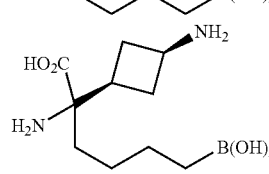
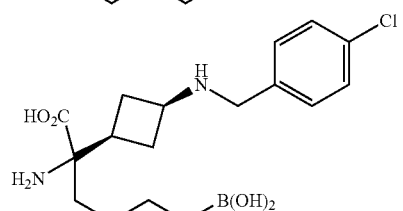
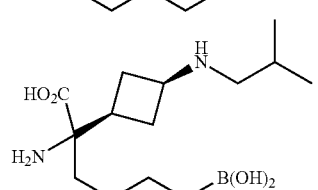
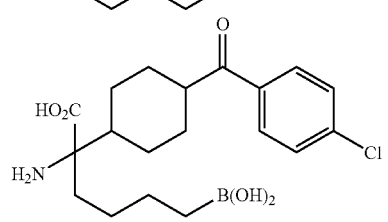
-continued
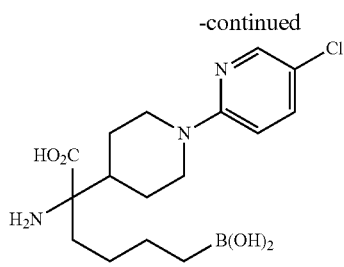
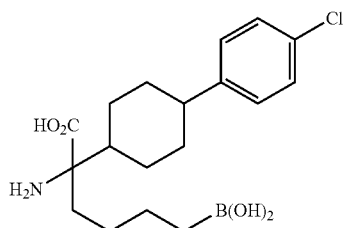
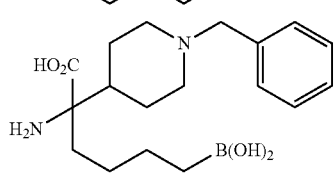
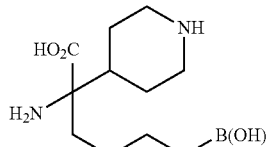
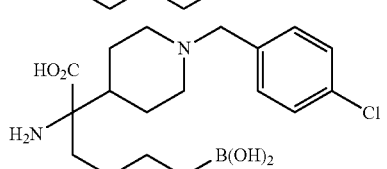
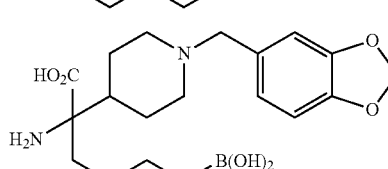
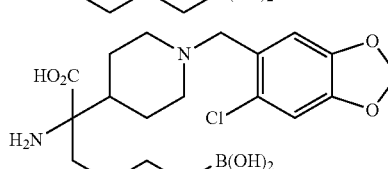
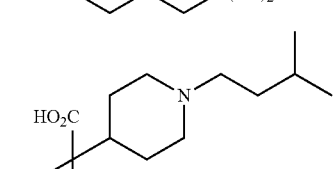
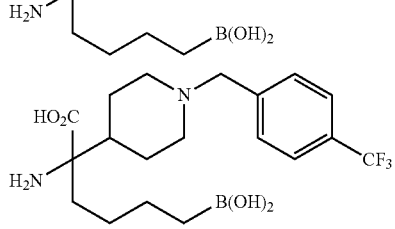

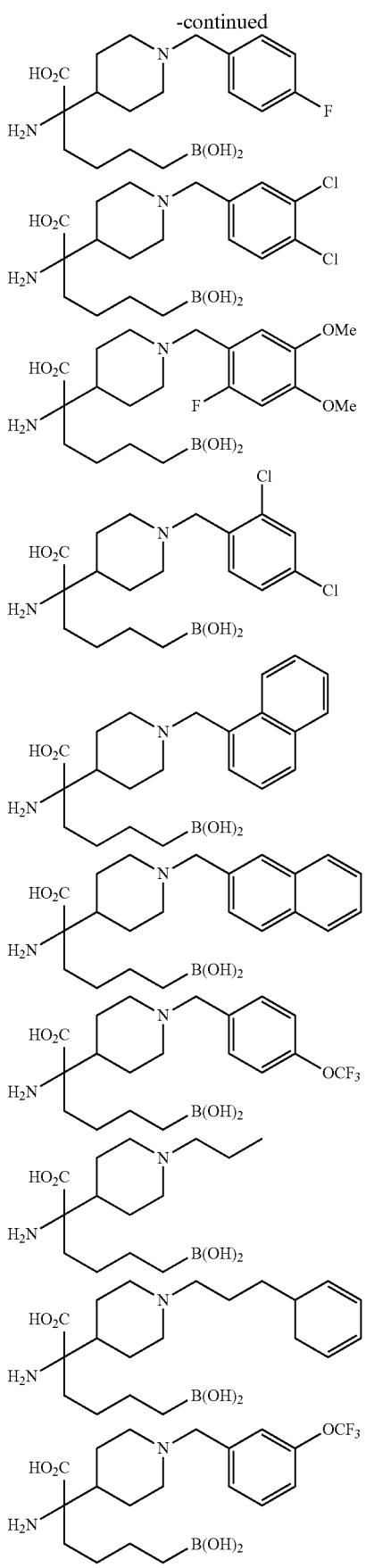

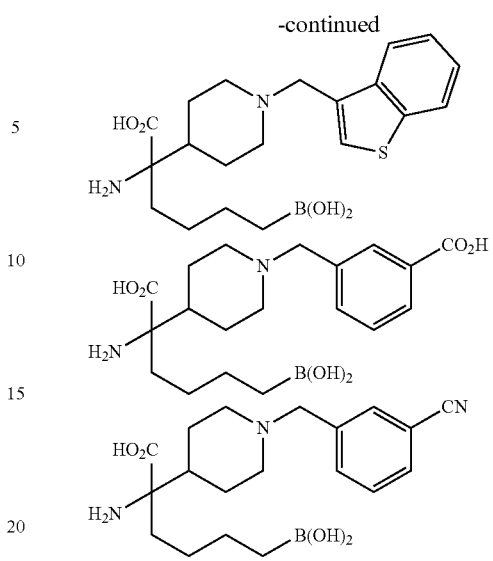

or a pharmaceutically acceptable salt, stereoisomer, or prodrug thereof.

In certain embodiments, the arginase inhibitor used in the methods of the invention is:

HOOC—CH(NH$_2$)—Y$_1$—Y$_2$—Y$_3$—Y$_4$—B(OH)$_2$;

wherein each of Y$_1$, Y$_2$, Y$_3$, and Y$_4$ is selected from CH$_2$, S, O, NH, and N-alkyl.

In certain embodiments, the arginase inhibitor used in the methods of the invention is a compound of formula IVa or IVb:

IVa

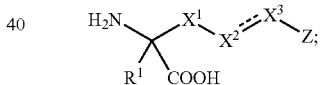

IVb or a stereoisomer, lactone prodrug, or pharmaceutically acceptable salt thereof,
wherein:
the dashed line represents an optional double bond;
Z is

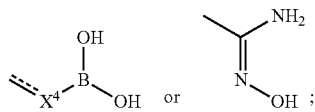

X$^1$ is —(CH$_2$)— or, when said double bond is present between X$^1$ and X$^2$, X$^1$ is —(CH)—;

X$^2$ is —(CH$_2$)— or —(NR$^2$)—, or, when said double bond is present between X$^1$ and X$^2$ or between X$^2$ and X$^3$, X$^2$ is —(CH)— or N;

X$^3$ is —(CH$_2$)—, a heteroatom moiety selected from the group consisting of —S—, —O— and —(NR$^2$)— or, when said double bond is present between X$^2$ and X$^3$ or between X$^3$ and X$^4$, X$^3$ is —(CH)— or N;

X$^4$ is —(CH$_2$)— or, when said double bond is present between X$^3$ and X$^4$, X$^4$ is —(CH)— and is in the trans configuration;

provided that not more than one of $X^2$ and $X^3$ is said —$(NR^2)$— or said heteroatom moiety;
provided that $X^3$ is —$(NR^2)$— when Z is

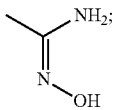

provided that there are no more than two double bonds between $X^1$, $X^2$, $X^3$, $X^4$ and no two double bonds share a common carbon atom;
$R^1$ is a monovalent moiety other than H; or $R^1$ and said α-carboxylate, when taken together, form a lactone; and
$R^2$ is, independently, H, methyl, or ethyl.

In certain embodiments, the arginase inhibitor used in the methods of the invention is a compound of formula V:

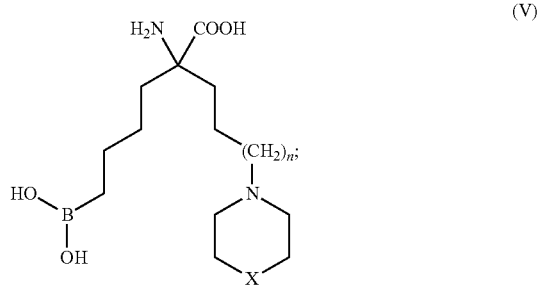

wherein:
n is 0, 1, or 2;
X is $NR^5$, $CR^6R^7$, O, S, $S(=O)$ or $S(O)_2$;
$R^7$ is H, OH, $OR^8$, CN or $NR^8R^9$; and
$R^5$, $R^6$, $R^8$ and $R^9$ are independently H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO$_2(C_1-C_6)$alkyl, —SO$_2$(aryl), —SO$_2$(heteroaryl), —CONH$(C_1-C_6)$alkyl, —CONH(aryl), or —CONH(heteroaryl);
or a derivative thereof, or a salt thereof.

Exemplary arginase inhibitors that may be used in the methods of the invention described herein include the compounds described in Appendix A, submitted herewith and hereby incorporated by reference.

In certain embodiments, the arginase inhibitor may be a prodrug of a compound of any of Formulae I, II, or III, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl or carboxylic acid).

In certain embodiments, arginase inhibitor compounds of the invention may be racemic. In certain embodiments, arginase inhibitor compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, a therapeutic preparation of the arginase inhibitor may be enriched to provide predominantly one enantiomer of a compound (e.g., of Formulae I, II, or III). An enantiomerically enriched mixture may comprise, for example, at least 60 mol percent of one enantiomer, or more preferably at least 75, 90, 95, or even 99 mol percent. In certain embodiments, the arginase inhibitor compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a arginase inhibitor composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of an arginase inhibitor compound (e.g., of Formulae I, II, or III). A diastereomerically enriched mixture may comprise, for example, at least 60 mol percent of one diastereomer, or more preferably at least 75, 90, 95, or even 99 mol percent.

Methods of Treatment

Several specific approaches to T-cell activation have shown considerable recent promise in the treatment of tumors. One such approach involves activation of T-cells by blockade of the T-cell surface antigen CTLA-4 by the antibody ipilimumab. A second approach is to prevent the activation of immune checkpoints by blocking the interaction of programmed cell death 1 protein, or PD-1, expressed on T-cells and its ligand, PD-L1 found on many tumors. A third approach is to activate the T-cell receptor by supplying key stimulating factors or nutrients such as tryptophan.

Inhibitors of indoleamine dioxygenase, or DO, have been shown to restore extracellular tryptophan without which the T-cell receptor cannot become active. Arginine, like tryptophan, is an amino acid that is fundamental to the function of cytotoxic T-cells. Without arginine, tumor-specific cytotoxic T-cells fail to express a functional T-cell receptor on their surface and as a result are unable to activate, proliferate, or mount an effective anti-tumor response. In response to tumor-secreted factors, myeloid-derived suppressor cells, or MDSCs, accumulate around the tumor and secrete the enzyme arginase, resulting in depletion of arginine from the tumor microenvironment.

Depletion of arginine due to elevated levels of arginase has been observed in renal cell carcinoma and acute myeloid leukemia. In addition, significant MDSC infiltrates have been observed in pancreatic, breast and other tumor types. Certain embodiments of the present invention provide a method of treating cancer by increasing arginine levels in a tumor microenvironment, thereby allowing activation of the body's cytotoxic T-cells. The arginine levels may be increased to at least twice the tumor arginine concentration. In certain such embodiments, the arginine levels in the microenvironment are increased at least 3-fold, 4-fold, 5-fold, 6-fold, 7-fold, 8-fold, 9-fold, 10-fold or greater, relative to the arginine level in the tumor.

One means of increasing arginine levels in the tumor microenvironment is by inhibiting arginase. Inhibitors of arginase may promote an anti-tumor immune response by restoring arginine levels, thereby allowing activation of the body's cytotoxic T-cells.

Accordingly, in certain embodiments, the invention provides methods for treating cancer, comprising administering to a subject in need thereof a therapeutically effective amount of an agent of arginine therapy.

In certain embodiments, the cancer that is treated by the methods of the invention is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer that is treated by the methods of the invention is a variety of acute myeloid leukemia (AML), breast cancer, colorectal cancer, chronic myelogenous leukemia (CML), esophageal cancer, gastric cancer, lung cancer, melanoma, non-small cell lung carcinoma (NSCLC), pancreatic cancer, prostate cancer, or renal cancer.

Combination therapy is an important treatment modality in many disease settings, such as cancer. Recent scientific advances have increased our understanding of the pathophysiological processes that underlie these and other complex diseases. This increased understanding has provided impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as arginase inhibitors.

When considering the administration of multiple therapeutic agents together, one must be concerned about what sort of drug interactions will be observed. This action can be positive (when the drug's effect is increased) or antagonistic (when the drug's effect is decreased) or a new side effect can be produced that neither produces on its own.

When the interaction causes an increase in the effects of one or both of the drugs the interaction, the degree to which the final effect of the combined drugs is greater than administering either drug alone can be calculated resulting in what is called the "combination index" (CI) (Chou and Talalay, 1984). A combination index at or around 1 is considered "additive"; whereas a value greater than 1 is considered "synergistic".

The present invention provides methods for combination therapy in treating or preventing cancer comprising an agent of arginine therapy (e.g., an arginase inhibitor) and one or more additional chemotherapeutic agents.

Certain embodiments of the invention relate to treating cancer comprising administering a chemotherapeutic agent and an arginase inhibitor.

In certain embodiments, the chemotherapeutic is an immune-stimulating agent.

The chemotherapeutic agent that may be conjointly administered with the agents of arginine therapy (e.g., arginase inhibitors) in the methods of the invention include aminoglutethimide, amsacrine, anastrozole, asparaginase, AZD5363, Bacillus Calmette-Guerin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In certain embodiments, the chemotherapeutic agent that may be administered with the agents of arginine therapy (e.g., arginase inhibitors) in the methods of the invention include abagovomab, adecatumumab, afutuzumab, anatumomab mafenatox, apolizumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

In certain embodiments, the chemotherapeutic agent is ipilimumab, nivolumab, pembrolizumab, or pidilizumab.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |

TABLE 1-continued

Exemplary combinatorial therapies for the treatment of cancer.

| Name | Therapeutic agents |
| --- | --- |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |

TABLE 1-continued

Exemplary combinatorial therapies for the treatment of cancer.

| Name | Therapeutic agents |
|---|---|
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/ cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/ MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjointly administered chemotherapeutic agent is selected from a metabolic enzyme inhibitor, such as glucose transporters, hexokinase, pyruvate kinase M2, lactate dehydrogenase 1 or 2, pyruvate dehydrogenase kinase, fatty acid synthase and glutaminase. In some embodiments, the inhibitor inhibits lactate dehydrogenase 1 or 2, or glutaminase. In certain embodiments, the inhibitor is CB-839.

In some embodiments, the conjointly administered chemotherapeutic agent is an immune-oncology therapeutic, such as an inhibitor of arginase, CTLA-4, indoleamine 2,3-dioxygenase, and/or PD-1/PD-L1. In certain embodiments, the immune-oncology agent is abagovomab, adecatumumab, afutuzumab, anatumomab mafenatox, apolizumab, blinatumomab, catumaxomab, durvalumab, epratuzumab, indoximod, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab. In some embodiments, the immune-oncology agent is indoximod, ipilimumab, nivolumab, pembrolizumab, or pidilizumab. In certain embodiments, the immune-oncology agent is ipilimumab.

In certain embodiments, the method of treating or preventing cancer further comprises administering one or more non-chemical methods of cancer treatment, such as radiation therapy, surgery, thermoablation, focused ultrasound therapy, cryotherapy, or a combination of the foregoing.

Cellular pathways operate more like webs than superhighways. There are multiple redundancies, or alternate routes, that are activated in response to the inhibition of a pathway. This redundancy promotes the emergence of resistant cells or organisms under the selective pressure of a targeted agent, resulting in drug resistance and clinical relapse.

In some cases, one can overcome immune evasion by the addition of another therapeutic agent. As demonstrated in FIG. 3, treatment of tumors with both an anticancer agent (e.g., anti-CTLA-4) and an arginase inhibitor resulted in a notable decrease in tumor growth. For this reason, combination therapies are often needed to effectively treat many tumors.

In certain embodiments of the invention, the chemotherapeutic agent is administered simultaneously with the arginase inhibitor. In certain embodiments, the chemotherapeutic agent is administered within about 5 minutes to within about 168 hours prior or after of the arginase inhibitor.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. C0 alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

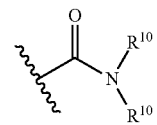

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

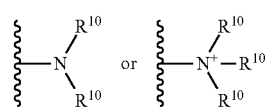

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

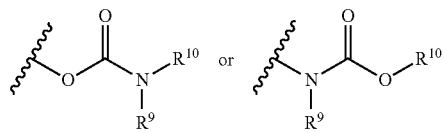

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

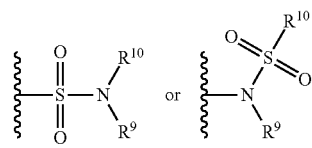

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

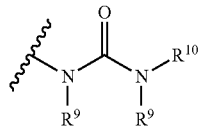

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula I, II, or III). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

In certain embodiments, the invention provides a pharmaceutical composition comprising a chemotherapeutic agent, and an arginase inhibitor, such as a compound of formula I, II, III, or a pharmaceutically acceptable salt thereof.

In certain embodiments, the present invention provides a pharmaceutical preparation suitable for use in a human patient, comprising a chemotherapeutic agent such as ipilimumab, nivolumab, pembrolizumab, or pidilizumab and any of the compounds shown above (e.g., an arginase inhibitor, such as a compound of formula I, II, or III), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present invention provides a pharmaceutical kit comprising a chemotherapeutic agent, such as ipilimumab, nivolumab, pembrolizumab, or pidilizumab, and a arginase inhibitor, such as a compound of formula I, II, III, or a pharmaceutically acceptable salt thereof, and optionally directions on how to administer the chemotherapeutic agent and arginase inhibitor.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I, II, or III) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I, II or III. As another example, the salt may comprise less than one inorganic or organic acid molecule per molecule of base, such as two molecules of compound of Formula I, II, or III per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Example 1: Tumor Pharmacodynamic Effects

LLC Study: Female C57.B1/6 mice were implanted subcutaneously with $1 \times 10^6$ Lewis Lung Carcinoma cells suspended in PBS.
4T1 Study: Female balb/c mice were implanted in the mammary fat pad with $1 \times 10^5$ 4 T1 mammary carcinoma cells suspended in PBS.
CT26 Study: Female balb/c mice were implanted subcutaneously with $1 \times 10^6$ CT26 colon carcinoma cells suspended in PBS.
B16 Study: Female C57.B1/6 mice were implanted subcutaneously with $2 \times 10^6$ B16 murine melanoma cells suspended in PBS.

On day 10-14 post-implant tumor bearing mice were randomized into groups of n=5 mice and treated with a single intraperitoneal dose of compound 190909 at 50 mg/kg IP or vehicle (phosphate buffered saline). Two hours post-dose, mice were sacrificed and tumors collected and flash frozen in liquid nitrogen. Arginine concentrations in tumor homogenates were determined by LC/MS/MS. Results are shown in FIG. 1.

Example 2: Tumor and Liver Multi-Day Pharmacodynamic Effects

Female balb/c mice were implanted in the mammary fat pad with $1 \times 10^5$ 4 T1 mammary carcinoma cells suspended in PBS. The day following implant groups of n=10 mice were dosed IP twice daily for 21 days with 1) Vehicle, phosphate buffered saline; 2) compound 190909 at 50 mg/kg; or 3) compound 190909 at 100 mg/kg. On Day 21, n=5 mice per groups were sacrificed at the trough time-point (~16 hrs following the previous dose), and the remaining n=5 mice per group received a final dose and were sacrificed two hours from the last dose. At sacrifice, tumor and liver were harvested and flash frozen in liquid nitrogen. Arginine concentrations in tumor and liver homogenates were determined by LC/MS/MS (FIG. 2)

Example 3: Single Agent Efficacy Study

Female C57.B1/6 mice (n=20) were implanted subcutaneously with $1 \times 10^6$ Lewis Lung Carcinoma cells suspended in PBS. The day following implantation, mice were randomized into 2 groups of n=10 mice to receive the following treatments dosed IP twice daily: 1) Vehicle (phosphate buffered saline); or 2) Compound 190909 at 100 mg/kg formulated in PBS. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. **P-value <0.01 (Two-sided T-test). Results are shown in FIG. 3 (left panel).

Example 4: Combination Therapy Efficacy Study

Female C57.B1/6 mice (n=40) were implanted subcutaneously with $1 \times 10^6$ Lewis Lung Carcinoma cells suspended in PBS. The day following implantation, mice were randomized into 4 groups of n=10 mice to receive the following treatments: 1) Vehicle (phosphate buffered saline) dosed IP twice daily; 2) Compound 190909 at 50 mg/kg formulated in PBS dosed IP twice daily; 3) anti CTLA-4 antibody clone 9H10 dosed at 5 mg/kg IP on days 2, 5, and 8; and 4) the combination of compound 190909 at 50 mg/kg IP BID and anti-CTLA-4 at 5 mg/kg on Days 2, 5, and 8. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. *P-value <0.05 (Two-sided T-test). Results are shown in FIG. 3 (right panel).

On Day 14, mice were sacrificed and tumors collected and placed into 10% neutral buffered formalin. Following overnight fixation, tumors were transferred to 70% ethanol. Tumors were embedded in paraffin, sectioned, and stained for CD3+ cells with an anti-CD3 polyclonal antibody (EMD Millipore PC630). Representative images from one animal from each group, as well as a graphical representation of the data, are presented in FIG. 4.

Example 5: Pharmacodynamic and Pharmacokinetic Protocol Including Arginine Measurement 1. Preparation of PD Stock Solutions at 10 mM in 1120

Accurately weigh 1.5-2.5 mg L-Arginine and Ornithine in a 2-ml glass vial. Add $H_2O$ to make 10 mM solution.

Tightly cap the vial. Vortex or agitate to completely dissolve the powder.

Label the vial accordingly. Store the stock solution at $-20°$ C.

2. Preparation of PK Stock Solution in DMSO

Accurate weigh 0.5-1.5 mg of CB-909 in a 2-ml glass vial. Add DMSO to make 1.0 mg free base/ml solution (conversion factor: 1.35).

Tightly cap the vial. Vortex or agitate to completely dissolve the powder.

Label the vial accordingly. Store the stock solution at −20° C.

3. Prepare PD Calibration Standards (STD)

Calibration standards are prepared at 7 concentrations (see table, below). After use/preparation, store the calibration standards at −80° C. and thaw them at room temperature before use. Stability is at least good for 2 months at −80° C.

| Test article conc. (µM) | working solution (WS) | WS volume (µL) | 2.5% BSA added (µL) |
|---|---|---|---|
| S1 | 500 | 10 mM Arg and 10 mM Orn | 10 uL (Arg) + 10 uL (Orn) | 180 |
| S2 | 150 | S1 | 30 | 70 |
| S3 | 50 | S1 | 10 | 90 |
| S4 | 15 | S2 | 10 | 90 |
| S5 | 5.0 | S3 | 10 | 90 |
| S6 | 1.5 | S4 | 10 | 90 |
| S7 | 0.5 | S5 | 10 | 90 |

4. Prepare PK Calibration Standards (STD)

Calibration standards are prepared freshly at 7 concentrations in corresponding biomatrix (e.g. one curve for plasma, one curve for liver). Add 10 uL of CB-909 stock solution (1.0 mg/mL) to 90 uL of $H_2O$ to make a 0.1 mg/mL working solution.

| Test article conc. (ng/mL) | working solution (WS) | WS volume (µL) | Matrix added (µL) |
|---|---|---|---|
| S1 | 5000 | 0.1 mg/mL | 10 | 190 |
| S2 | 1500 | S1 | 30 | 70 |
| S3 | 500 | S1 | 10 | 90 |
| S4 | 150 | S2 | 10 | 90 |
| S5 | 50 | S3 | 10 | 90 |
| S6 | 15 | S4 | 10 | 90 |
| S7 | 5.0 | S5 | 10 | 90 |

5. Prepare Tissue Homogenates

A pre-cold (0° C.) solution of 25% ACN with 0.1% TFA was added to the tissue samples (10 µL solution/mg tissue), and then homogenized twice using a Tissuelyser II homogenizer at 4° C. for 4 min (Frequency 20 1/s, tumor samples may need more times).

6. Plasma/Tissue Sample Processing by Protein Precipitation in 80% ACN with 0.1% TFA (or 10% TCA)

Take 30 µL of calibration standard, plasma or tissue homogenate sample, mixed with 90 µL extraction solution with IS (80% ACN with 0.1% TFA).

Vortex and centrifuge for 10 minutes at 5000 RPM.

Transfer 30 µL of the supernatant to 90 µL of 0.1% FA in a 96-well plate.

7. LC-MS Method

HPLC column: Agilent Zorbax SB-C18, 3.0 um, 3×100 mm

Solvent A: H2O/0.1% FA

Solvent B: AcN/0.1% FA

Flow rate: 0.5 ml/min

Injection volume: 10 uL

| Gradient: | 0.5 min | 3% B |
|---|---|---|
| | 1.5 min | 15% B |
| | 2.0 min | 95% B |
| | 3.2 min | 95% B |
| | 3.3 min | 3% B |
| | 4.5 min | STOP |

MRM Conditions:

| analyte | Q1 | Q3 | DP | EP | CE | CXP |
|---|---|---|---|---|---|---|
| CB-909 | 314.0 | 278.1 | 61 | 10 | 21 | 14 |
| CB-900 | 287.2 | 251.2 | 51 | 10 | 25 | 6 |
| Arginine | 175.2 | 70.1 | 76 | 10 | 35 | 12 |
| Ornithine | 133.0 | 70.0 | 46 | 10 | 25 | 4 |
| C13-Arg | 181.2 | 74.0 | 56 | 10 | 33 | 4 |
| C13-Orn | 138.1 | 74.1 | 41 | 10 | 25 | 4 |

MS Source Conditions:

CUR: 200, CAD: low, IS: 5500, TEM: 500, GS1: 80, GS2: 40

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

In particular, suitable compounds for practicing the invention are described in U.S. Patent Application Publication Nos. 2014/0343019, 2012/0083469, 2014/0371175, 2012/0129806, 2015/0080341, and PCT Application Publication Nos. WO 99/19295, WO 2010/085797, and WO 2012/091757, which are hereby incorporated by reference herein in their entirety.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of increasing the tumor-killing activity of cytotoxic T-cells in a tumor of a cancer patient, comprising conjointly administering to the patient an anti-cytotoxic T-lymphocyte-associated protein 4 (anti-CTLA-4) antibody and an arginase inhibitor, wherein the arginase inhibitor is a compound having the structure

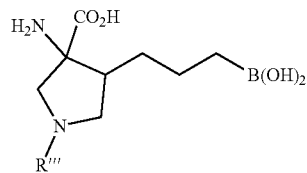

wherein
R''' is selected from H, OH, —S(O)R$^d$, —S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)NR$^d$R$^e$, -C(O)(C$_1$-C$_6$)alkyl, -C(O)(C$_3$-C$_{14}$)aryl, —C(O)/O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, —C(O)(C$_3$-C$_{14}$)heterocycloalkyl, (C$_3$-C$_{14}$)heteroaryl, (C$_3$-C$_{14}$)aryl-(C$_1$-C$_6$)alkylene-, (C$_3$-C$_6$)cycloalkyl-(C$_1$-C$_6$)alkylene-, (C$_3$-C$_{14}$)heteroaryl-(C$_1$-C$_6$)alkylene- and (C$_3$-C$_{14}$)heterocycle-(C$_1$-C$_6$)alkylene-;

wherein any alkyl, alkylene, aryl, heteroaryl, cycloalkyl, or heterocycloalkyl is optionally substituted with one or more members selected from halogen, oxo, —COOH, —CN, —NO$_2$, —NR$^d$R$^e$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy; and wherein R$^d$, R$^e$, R$^g$, R$^h$ are each independently selected from H, straight or branched (C$_1$-C$_6$)alkyl, (C$_3$-C$_{14}$)aryl(C$_1$-C$_6$)alkylene-, (C$_3$-C$_{14}$)aryl, (C$_1$-C$_6$)hydroxyalkyl, (C$_1$-C$_6$)aminoalkyl, H$_2$N(C$_1$-C$_6$)alkylene-, (C$_3$-C$_6$)cycloalkyl, (C$_3$-C$_{14}$)heterocycloalkyl (C$_3$-C$_{14}$)heteroaryl (C$_3$-C$_{14}$)aryl-(C$_1$-C$_6$)alkylene-, and (C$_3$-C$_6$)aryl-(C$_3$-C$_{14}$)-cycloalkylene-, or a pharmaceutically acceptable salt thereof.

2. The method of claim 1, wherein
R''' is selected from H, OH, —S(O)R$^d$, —S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)(C$_1$-C$_6$)alkyl, —C(O)(C$_3$-C$_{14}$)aryl, —C(O)O(C$_1$-C$_6$)alkyl, —C(O)(C$_3$-C$_{14}$)aryl, (C$_3$-C$_6$)cycloalkyl, (C$_3$-C$_{14}$)heterocycloalkyl, —C(O)(C$_3$-C$_{14}$)heterocycloalkyl, (C$_3$-C$_{14}$)heteroaryl, (C$_3$-C$_{14}$)aryl-(C$_1$-C$_6$)alkylene-, (C$_3$-C$_6$)cycloalkyl-(C$_1$-C$_6$)alkylene-, (C$_3$-C$_{14}$)heteroaryl-(C$_1$-C$_6$)alkylene- and (C$_3$-C$_{14}$)heterocycle-(C$_1$-C$_6$)alkylene-;

wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy; and wherein R$^d$, R$^e$, R$^g$, and R$^h$ are each independently selected from H, straight or branched (C$_1$-C$_6$)alkyl, (C$_3$-C$_{14}$)aryl(C$_1$-C$_6$)alkylene-, (C$_3$-C$_{14}$)aryl, (C$_1$-C$_6$)hydroxyalkyl, (C$_1$-C$_6$)aminoalkyl, H$_2$N(C$_1$-C$_6$)alkylene-, (C$_3$-C$_6$)cycloalkyl, (C$_3$-C$_{14}$)heterocycloalkyl, (C$_3$-C$_{14}$)heteroaryl, (C$_3$-C$_{14}$)aryl-(C$_1$-C$_6$)alkylene-, and (C$_3$-C$_6$)aryl ,(C$_3$-C$_{14}$)-cycloalkylene-.

3. The method of claim 1, wherein
R''' is selected from —C(O)(C$_1$-C$_6$)alkyl, —C(O)O(C$_1$-C$_6$)alkyl, —C(O)(C$_3$-C$_{14}$)heterocycloalkyl and —C(O)(C$_3$-C$_{14}$)aryl;

wherein any alkyl, aryl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy; and wherein R$^d$, R$^e$, R$^g$, and R$^h$ are each independently selected from H, straight or branched (C$_1$-C$_6$)alkyl, (C$_3$-C$_{14}$)aryl(C$_1$-C$_6$)alkylene-, (C$_3$-C$_{14}$)aryl, (C$_1$-C$_6$)hydroxyalkyl, (C$_1$-C$_6$)aminoalkyl, H$_2$N(C$_1$-C$_6$)alkylene-, (C$_3$-C$_6$)cycloalkyl, (C$_3$-C$_{14}$)heterocycloalkyl (C$_3$-C$_{14}$)heteroaryl, (C$_3$-C$_{14}$)aryl-(C$_1$-C$_6$)alkylene-, and (C$_3$-C$_6$)aryl-(C$_3$-C$_{14}$)-cycloalkylene-.

4. The method of claim 1, wherein the arginase inhibitor is a compound having the structure

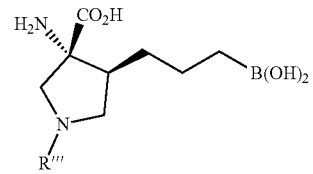

or a pharmaceutically acceptable salt thereof.

5. The method of claim 4, wherein
R''' is selected from OH, —S(O)R$^d$, —S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)(C$_1$-C$_6$)alkyl, —C(O)(C$_3$-C$_{14}$)aryl, —C(O)O(C$_1$-C$_6$)alkyl, -C(O)O(C$_3$-C$_{14}$)aryl, (C$_3$-C$_6$)cycloalkyl, (C$_3$-C$_{14}$)heterocycloalkyl, —C(O)(C$_3$-C$_{14}$)heterocycloalkyl, (C$_3$-C$_{14}$)heteroaryl, (C$_3$-C$_{14}$)aryl-(C$_1$-C$_6$)alkylene-, (C$_3$-C$_6$)cycloalkyl-(C$_1$-C$_6$)alkylene-, (C$_3$-C$_{14}$)heteroaryl-(C$_1$-C$_6$)alkylene- and (C$_3$-C$_{14}$)heterocycle-(C$_1$-C$_6$)alkylene-;

wherein any alkyl, alkylene, aryl, heteroaryl, cycloalkyl, or heterocycloalkyl is optionally substituted with one or more members selected from halogen, oxo, —COON, —CN, —NO$_2$, —OH, —NR$^d$R$^r$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy; and wherein R$^d$, R$^e$, R$^g$, and R$^h$ are each independently selected from H, straight or branched (C$_1$-C$_6$)alkyl, (C$_3$-C$_{14}$)aryl(C$_1$-C$_6$)alkylene-, (C$_3$-C$_{14}$)aryl, (C$_1$-C$_6$)hydroxyalkyl, (C$_1$-C$_6$)aminoalkyl, H$_2$N(C$_1$-C$_6$)alkylene-, (C$_3$-C$_6$)cycloalkyl, (C$_3$-C$_{14}$)heterocycloalkyl, (C$_3$-C$_{14}$)heteroaryl, (C$_3$-C$_{14}$)aryl-(C$_1$-C$_6$)alkylene-, and (C$_3$-C$_6$)aryl-(C$_3$-C$_{14}$)-cycloalkylene-.

6. The method of claim 4, wherein
R''' is selected from —C(O)(C$_1$-C$_6$)alkyl, —C(O)O(C$_1$-C$_6$)alkyl, —C(O)(C$_3$-C$_{14}$)heterocycloalkyl and —C(O)(C$_3$-C$_{14}$)aryl;

wherein any alkyl, aryl, or heterocycloalkyl is optionally substituted with one or more members selected from halogen, oxo, —COOH, —CN, —NO$_2$, —NR$^d$R$^e$, —NR$^g$S(O)$_2$R$^h$, (C$_1$-C$_6$)alkoxy, (C$_3$-C$_{14}$)aryl, (C$_1$-C$_6$)haloalkyl and (C$_3$-C$_{14}$)aryloxy; and wherein R$^d$, R$^e$, R$^g$, and R$^h$ are each independently selected from H, straight or branched (C$_1$-C$_6$)alkyl, (C$_3$-C$_{14}$)aryl(C$_1$-C$_6$)alkylene-, (C$_3$-C$_{14}$)aryl, (C$_1$-C$_6$)hydroxyalkyl, (C$_1$-C$_6$)aminoalkyl, H$_2$N(C$_1$-C$_6$)alkylene-, (C$_3$-C$_6$)cycloalkyl, (C$_3$-C$_{14}$)heterocycloalkyl, (C$_3$-C$_{14}$)eteroaryl, (C$_3$-C$_{14}$)aryl-(C$_1$-C$_6$)alkylene-, and (C$_3$-C$_6$)aryl-(C$_3$-C$_{14}$)-cycloalkylene-.

7. A method of increasing the tumor-killing activity of cytotoxic T-cells in a tumor of a cancer patient, comprising conjointly administering to the patient a pharmaceutical composition that provides an anti-CTLA-4 antibody and a pharmaceutical composition that provides an arginase inhibitor as defined in claim 6.

8. The method of claim 4, wherein the anti-CTLA-4 antibody is administered from 5 minutes to 168 hours prior to administration of the arginase inhibitor.

9. The method of claim 4, wherein the anti-CTLA-4 antibody is ipilimumab.

10. The method of claim 4, wherein the anti-CTLA-4 antibody is tremelimumab.

11. The method of claim 4, wherein the patient has lung cancer.

12. The method of claim 4, wherein the patient has colon cancer.

13. The method of claim 4, wherein the patient has melanoma.

14. The method of claim 4, wherein the patient has breast cancer.

15. The method of claim 4, wherein the patient has non-small cell lung cancer.

16. The method of claim 4, wherein the patient has colorectal cancer.

17. The method of claim 4, wherein the patient has bladder cancer.

18. The method of claim 4, wherein the patient has gastric cancer.

19. The method of claim 4, wherein the patient has head and neck cancer.

20. The method of claim 4, wherein the patient has mesothelioma.

21. The method of claim 4, wherein the patient has bile duct cancer.

22. The method of claim 4, wherein the patient has ovarian cancer.

23. The method of claim 4, wherein the patient has multiple myeloma.

24. The method of claim 4, wherein the patient has endometrial cancer.

25. The method of claim 4, wherein the patient has esophageal cancer.

26. A method of increasing the tumor-killing activity of cytotoxic T-cells in a tumor of a cancer patient, comprising conjointly administering to the patient a pharmaceutical composition that provides an anti-CTLA-4 antibody and a pharmaceutical composition that provides an arginase inhibitor as defined in claim 4.

27. The method of claim 26, wherein the pharmaceutical composition that provides the CTLA I inhibitor anti-CTLA-4 antibody is administered from 5 minutes to 168 hours prior to administration of the pharmaceutical composition that provides the arginase inhibitor.

28. The method of claim 26, wherein the anti-CTLA-4 antibody is ipilimumab.

29. The method of claim 26, wherein the anti-CTLA-4 antibody is tremelimumab.

30. A method of increasing the tumor-killing activity of cytotoxic T-cells in a tumor of a cancer patient, comprising conjointly administering to the patient a pharmaceutical composition that provides an anti-CTLA-4 antibody and a pharmaceutical composition that provides an arginase inhibitor as defined in claim 1.

* * * * *